(12) United States Patent
Avelar et al.

(10) Patent No.: US 9,955,962 B2
(45) Date of Patent: May 1, 2018

(54) SUTURE DELIVERY TOOLS FOR ENDOSCOPIC AND ROBOT-ASSISTED SURGERY AND METHODS

(75) Inventors: Rui Avelar, Goleta, CA (US); Lev Drubetsky, Coquitlam (CA); Alexander Naimagon, Richmond (CA)

(73) Assignees: Ethicon, Inc., Somerville, NJ (US); Ethicon LLC, Guaynabo, PR (US)

( * ) Notice: Subject to any disclaimer, the term of this patent is extended or adjusted under 35 U.S.C. 154(b) by 1311 days.

(21) Appl. No.: 13/814,171

(22) PCT Filed: Jun. 10, 2011

(86) PCT No.: PCT/US2011/040014
§ 371 (c)(1),
(2), (4) Date: Sep. 30, 2013

(87) PCT Pub. No.: WO2011/156733
PCT Pub. Date: Dec. 15, 2011

(65) Prior Publication Data
US 2014/0039527 A1 Feb. 6, 2014

Related U.S. Application Data

(60) Provisional application No. 61/354,009, filed on Jun. 11, 2010.

(51) Int. Cl.
*A61B 17/04* (2006.01)
*A61B 17/12* (2006.01)
(Continued)

(52) U.S. Cl.
CPC ........ *A61B 17/04* (2013.01); *A61B 17/06128* (2013.01); *A61B 17/06166* (2013.01);
(Continued)

(58) Field of Classification Search
CPC .......... A61B 2017/06142; A61B 2017/06057; A61B 2017/06176; A61B 2017/0409;
(Continued)

(56) References Cited

U.S. PATENT DOCUMENTS 709,392 A   9/1902   Brown
733,723 A   7/1903   Lukens
(Continued)

FOREIGN PATENT DOCUMENTS

BE   1014364   9/2003
CA   2309844   12/1996
(Continued)

OTHER PUBLICATIONS

US 8,663,276, 03/2014, Leung et al. (withdrawn)
(Continued)

*Primary Examiner* — Katherine M Shi
(74) *Attorney, Agent, or Firm* — Frost Brown Todd LLC

(57) ABSTRACT

A suture delivery tool releasably secures a self-retaining suture to permit delivery of the self-retaining suture to a surgical site in a patient through an access port. Suture delivery tools are disclosed suitable for manual operation and operation using robotically-assisted surgical systems. In some embodiments, a suture spool is part of a cartridge which is releasably attached to the suture delivery tool. Cartridges is, in some embodiments, replaced after deployment of the self-retaining suture and different cartridges having different self-retaining suture are, in some embodiments, selected and attached to the suture delivery tool as required for a procedure.

8 Claims, 15 Drawing Sheets

(51) Int. Cl.
  *A61B 17/06* (2006.01)
  *A61B 90/96* (2016.01)
  *A61B 34/35* (2016.01)
  *A61B 34/00* (2016.01)
  *A61B 90/98* (2016.01)
  *A61B 17/064* (2006.01)
  *A61B 17/34* (2006.01)
  *A61B 34/30* (2016.01)
  *A61B 90/00* (2016.01)

(52) U.S. Cl.
  CPC .............. *A61B 34/30* (2016.02); *A61B 34/35* (2016.02); *A61B 34/74* (2016.02); *A61B 34/76* (2016.02); *A61B 90/96* (2016.02); *A61B 90/98* (2016.02); *A61B 17/0644* (2013.01); *A61B 17/3421* (2013.01); *A61B 2017/0406* (2013.01); *A61B 2017/0412* (2013.01); *A61B 2017/0417* (2013.01); *A61B 2017/06057* (2013.01); *A61B 2017/06142* (2013.01); *A61B 2017/06176* (2013.01); *A61B 2034/302* (2016.02); *A61B 2090/036* (2016.02)

(58) Field of Classification Search
  CPC ........ A61B 17/06114; A61B 17/06123; A61B 17/06128
  USPC ....... 206/63.3, 339, 380; 606/139, 144, 146, 606/232
  See application file for complete search history.

(56) References Cited

U.S. PATENT DOCUMENTS

| | | |
|---|---|---|
| 816,026 A | 3/1906 | Meier |
| 879,758 A | 2/1908 | Foster |
| 1,142,510 A | 6/1915 | Engle |
| 1,248,825 A | 12/1917 | Dederer |
| 1,321,011 A | 11/1919 | Cottes |
| 1,558,037 A | 10/1925 | Morton |
| 1,728,316 A | 9/1929 | Von Wachenfeldt |
| 1,886,721 A | 11/1932 | O'Brien |
| 2,094,578 A | 10/1937 | Blumenthal et al. |
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,591,063 A | 4/1952 | Goldberg |
| 2,684,070 A | 7/1954 | Kelsey |
| 2,736,964 A | 3/1956 | Lieberman |
| 2,779,083 A | 1/1957 | Enton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski et al. |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,123,077 A | 3/1964 | Alcamo |
| 3,136,418 A | 6/1964 | Stacy et al. |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,376,973 A * | 4/1968 | Granowitz ....... A61B 17/06123 206/63.3 |
| 3,378,010 A | 4/1968 | Codling |
| 3,385,299 A | 5/1968 | LeRoy |
| 3,394,704 A | 7/1968 | Dery |
| 3,494,006 A | 2/1970 | Brumlik |
| 3,522,637 A | 8/1970 | Brumlik |
| 3,525,340 A | 8/1970 | Gilbert |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,716,058 A | 2/1973 | Tanner, Jr. |
| 3,720,055 A | 3/1973 | de Mestral et al. |
| 3,748,701 A | 7/1973 | De Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,951,261 A | 4/1976 | Mandel et al. |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen et al. |
| 3,990,144 A | 11/1976 | Schwartz |
| 4,006,747 A | 2/1977 | Kronenthal |
| 4,008,303 A | 2/1977 | Glick et al. |
| 4,014,434 A | 3/1977 | Thyen |
| 4,027,608 A | 6/1977 | Arbuckle |
| 4,043,344 A | 8/1977 | Landi |
| 4,052,988 A | 10/1977 | Doddi et al. |
| 4,063,638 A | 12/1977 | Marwood |
| D246,911 S | 1/1978 | Bess, Jr. et al. |
| 4,069,825 A | 1/1978 | Akiyama |
| 4,073,298 A | 2/1978 | Le Roy |
| 4,135,623 A | 1/1979 | Thyen et al. |
| 4,137,921 A | 2/1979 | Okuzumi et al. |
| 4,182,340 A | 1/1980 | Spencer |
| 4,183,431 A | 1/1980 | Schmidt et al. |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,253,563 A | 3/1981 | Komarnycky |
| 4,259,959 A | 4/1981 | Walker |
| 4,278,374 A | 7/1981 | Wolosianski |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey |
| 4,434,796 A | 3/1984 | Karapetian |
| 4,449,298 A | 5/1984 | Patz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |

(56) References Cited

U.S. PATENT DOCUMENTS

| | | |
|---|---|---|
| 4,496,045 A | 1/1985 | Ferguson et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,712,553 A | 12/1987 | MacGregor |
| 4,719,917 A | 1/1988 | Barrows |
| 4,741,330 A | 5/1988 | Hayhurst |
| 4,750,910 A | 6/1988 | Takayanagi et al. |
| 4,776,337 A | 10/1988 | Palmaz |
| 4,813,537 A | 3/1989 | Okuhara et al. |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuck et al. |
| 4,930,945 A | 6/1990 | Arai et al. |
| 4,932,962 A | 6/1990 | Yoon et al. |
| 4,946,043 A | 8/1990 | Roshdy et al. |
| 4,946,468 A | 8/1990 | Li |
| 4,948,444 A | 8/1990 | Schultz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,089,012 A | 2/1992 | Prou |
| 5,101,968 A | 4/1992 | Henderson et al. |
| 5,102,418 A | 4/1992 | Granger et al. |
| 5,102,421 A | 4/1992 | Anpach, Jr. |
| 5,103,073 A | 4/1992 | Danilov et al. |
| 5,112,344 A | 5/1992 | Petros |
| 5,121,836 A | 6/1992 | Brown et al. |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,131,534 A | 7/1992 | Brown et al. |
| 5,133,738 A | 7/1992 | Korthoff et al. |
| 5,141,520 A | 8/1992 | Goble et al. |
| 5,147,382 A | 9/1992 | Gertzman et al. |
| 5,154,283 A | 10/1992 | Brown |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,249,673 A | 10/1993 | Sinn |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,341,922 A | 8/1994 | Cerwin et al. |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,386,912 A | 2/1995 | Holzwarth et al. |
| 5,391,173 A | 2/1995 | Wilk |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,362 A | 8/1995 | Sinn |
| 5,437,680 A | 8/1995 | Yoon et al. |
| 5,450,860 A | 9/1995 | O'Connor |
| 5,451,461 A | 9/1995 | Broyer |
| 5,460,263 A | 10/1995 | Brown et al. |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,344 A | 12/1995 | Stone et al. |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,494,154 A | 2/1996 | Ainsworth et al. |
| 5,500,000 A | 3/1996 | Feagin et al. |
| 5,500,991 A | 3/1996 | Demarest et al. |
| 5,503,266 A | 4/1996 | Kalbfeld et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |

(56) References Cited

U.S. PATENT DOCUMENTS

| | | |
|---|---|---|
| 5,531,760 A | 7/1996 | Alwafaie |
| 5,531,761 A | 7/1996 | Yoon |
| 5,531,790 A | 7/1996 | Frechet et al. |
| 5,533,611 A | 7/1996 | Bordighon et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,566,821 A | 10/1996 | Brown et al. |
| 5,566,822 A | 10/1996 | Scanlon |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup, III et al. |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,654 A | 9/1997 | Thompson |
| 5,662,714 A | 9/1997 | Charvin et al. |
| 5,669,935 A | 9/1997 | Rosenman et al. |
| 5,676,675 A | 10/1997 | Grice |
| D386,583 S | 11/1997 | Ferragamo et al. |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,715,942 A | 2/1998 | Li et al. |
| 5,716,358 A | 2/1998 | Ochoa et al. |
| 5,716,376 A | 2/1998 | Roby |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Beyar et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,871,089 A | 2/1999 | Odermatt |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,918,733 A | 7/1999 | Cerwin et al. |
| 5,919,234 A | 7/1999 | Lemperle et al. |
| 5,921,982 A | 7/1999 | Lesh et al. |
| 5,925,078 A | 7/1999 | Anderson |
| 5,931,855 A | 8/1999 | Buncke |
| 5,935,138 A | 8/1999 | McJames, II et al. |
| 5,938,668 A | 8/1999 | Scirica et al. |
| 5,941,899 A | 8/1999 | Granger et al. |
| 5,950,505 A | 9/1999 | Locher |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 5,997,554 A | 12/1999 | Thompson |
| 6,001,111 A | 12/1999 | Sepetka et al. |
| 6,012,216 A | 1/2000 | Esteves et al. |
| 6,015,042 A | 1/2000 | Cerwin et al. |
| 6,015,410 A | 1/2000 | Tormala et al. |
| 6,024,757 A | 2/2000 | Haase et al. |
| 6,027,523 A | 2/2000 | Schmieding |
| 6,029,806 A | 2/2000 | Cerwin et al. |
| 6,039,741 A | 3/2000 | Meislin |
| 6,042,583 A | 3/2000 | Thompson et al. |
| 6,045,571 A | 4/2000 | Hill et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,254,616 B1 | 7/2001 | Wright |
| 6,260,696 B1 | 7/2001 | Braginsky et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,784 B1 * | 11/2001 | Djurovic .......... A61B 17/06109 606/146 |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,463,719 B2 | 10/2002 | Dey et al. |
| 6,471,715 B1 | 10/2002 | Weiss |

(56) References Cited

U.S. PATENT DOCUMENTS

| | | |
|---|---|---|
| 6,478,809 B1 | 11/2002 | Brotz |
| 6,481,569 B1 | 11/2002 | Alpern |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,659,270 B2 | 12/2003 | Williamson, IV |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,739,450 B2 | 5/2004 | Roshdy et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Geonva et al. |
| 6,852,825 B2 | 2/2005 | Ledlein et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,938,755 B2 | 9/2005 | Braginsky et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,037,984 B2 | 5/2006 | Ledlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Shuldt-Hempe et al. |
| 7,156,862 B2 | 1/2007 | Jacobs et al. |
| 7,160,312 B2 | 1/2007 | Saadat |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,329,271 B2 | 2/2008 | Koyfman et al. |
| 7,371,253 B2 | 5/2008 | Leung et al. |
| 7,381,211 B2 | 6/2008 | Zamierowski |
| 7,513,904 B2 | 4/2009 | Sulamanidze et al. |
| 7,582,105 B2 | 9/2009 | Kolster |
| 7,600,634 B2 | 10/2009 | Malinowski et al. |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,871,425 B2 | 1/2011 | Jones et al. |
| 7,879,072 B2 | 2/2011 | Bonutti et al. |
| 7,919,112 B2 | 4/2011 | Pathak et al. |
| 7,976,469 B2 | 7/2011 | Bonde et al. |
| 8,083,770 B2 | 12/2011 | Ruff et al. |
| 8,100,940 B2 | 1/2012 | Leung et al. |
| 8,118,834 B1 | 2/2012 | Goraltchouk et al. |
| 8,216,273 B1 | 7/2012 | Goraltchouk et al. |
| 8,225,673 B2 | 7/2012 | D'Agostino |
| 8,226,684 B2 | 7/2012 | Nawrocki et al. |
| 8,246,652 B2 | 8/2012 | Ruff |
| 8,308,761 B2 | 11/2012 | Brailovski et al. |
| 8,459,446 B2 | 6/2013 | Kozlowski |
| 8,460,338 B2 | 6/2013 | Goraltchouk et al. |
| 8,480,686 B2 * | 7/2013 | Bakos ............... A61B 17/0401 606/139 |
| 8,615,856 B1 | 12/2013 | Gelbart |
| 8,641,732 B1 | 2/2014 | Goraltchouk et al. |
| 8,652,170 B2 | 2/2014 | Leung et al. |
| 8,679,158 B2 | 3/2014 | Leung et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |

(56) References Cited

U.S. PATENT DOCUMENTS

| | | |
|---|---|---|
| 2001/0039450 A1 | 11/2001 | Pavcnik et al. |
| 2001/0051807 A1 | 12/2001 | Grafton |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0077448 A1 | 6/2002 | Antal et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173822 A1 | 11/2002 | Justin et al. |
| 2002/0179718 A1 | 12/2002 | Murokh et al. |
| 2003/0040795 A1 | 2/2003 | Elson et al. |
| 2003/0052028 A1 | 3/2003 | Lei |
| 2003/0069602 A1 | 4/2003 | Jacobs et al. |
| 2003/0088270 A1 | 5/2003 | Lubbers et al. |
| 2003/0149447 A1 | 8/2003 | Morency |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1* | 10/2003 | Keane ............... A61B 17/0401 606/146 |
| 2003/0225424 A1 | 12/2003 | Benderev |
| 2003/0229361 A1 | 12/2003 | Jackson |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0030354 A1* | 2/2004 | Leung ............... A61B 17/0401 606/232 |
| 2004/0039415 A1 | 2/2004 | Zamierowski |
| 2004/0049224 A1 | 3/2004 | Buehlmann et al. |
| 2004/0050721 A1 | 3/2004 | Roby et al. |
| 2004/0059370 A1 | 3/2004 | Greene, Jr. et al. |
| 2004/0059377 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0230223 A1 | 11/2004 | Bonutti et al. |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 6/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Young et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Ledlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0016251 A1 | 1/2007 | Roby |
| 2007/0021779 A1 | 1/2007 | Garvin et al. |
| 2007/0027475 A1 | 2/2007 | Pagedas |

(56) References Cited

U.S. PATENT DOCUMENTS

| | | |
|---|---|---|
| 2007/0038249 A1 | 2/2007 | Kolster |
| 2007/0065663 A1 | 3/2007 | Trull et al. |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0185494 A1 | 8/2007 | Reese |
| 2007/0187861 A1 | 8/2007 | Pageneva et al. |
| 2007/0208355 A1 | 9/2007 | Ruff |
| 2007/0208377 A1 | 9/2007 | Kaplan et al. |
| 2007/0213744 A1 | 9/2007 | Farris |
| 2007/0213770 A1 | 9/2007 | Pj Drefyss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0225764 A1 | 9/2007 | Benavitz et al. |
| 2007/0227914 A1 | 10/2007 | Cerwin et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0128296 A1 | 6/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0255612 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2008/0312688 A1 | 12/2008 | Naworocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0228021 A1 | 9/2009 | Leung |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250356 A1 | 10/2009 | Kirsch et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2010/0021516 A1 | 1/2010 | McKay |
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0140115 A1 | 6/2010 | Kirsch |
| 2010/0160961 A1 | 6/2010 | Nawrocki et al. |
| 2010/0163056 A1 | 7/2010 | Tschopp et al. |
| 2010/0170812 A1 | 7/2010 | Odierno |
| 2010/0211097 A1 | 8/2010 | Hadba et al. |
| 2010/0211098 A1 | 8/2010 | Hadba et al. |
| 2010/0230300 A1 | 9/2010 | Hunter et al. |
| 2010/0239635 A1 | 9/2010 | McClain et al. |
| 2010/0292718 A1 | 11/2010 | Sholev et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298639 A1 | 11/2010 | Leung et al. |
| 2010/0298848 A1 | 11/2010 | Leung et al. |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298874 A1 | 11/2010 | Leung et al. |
| 2010/0298875 A1 | 11/2010 | Leung et al. |
| 2010/0298876 A1 | 11/2010 | Leung et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2010/0318124 A1 | 12/2010 | Leung et al. |
| 2011/0009902 A1 | 1/2011 | Leung et al. |
| 2011/0022086 A1 | 1/2011 | D'Agostino et al. |
| 2011/0046668 A1 | 2/2011 | Goraltchouk et al. |
| 2011/0046669 A1 | 2/2011 | Goraltchouk et al. |
| 2011/0056859 A1 | 3/2011 | Kozlowski |
| 2011/0093010 A1 | 4/2011 | Genova et al. |
| 2011/0106152 A1 | 5/2011 | Kozlowski |
| 2011/0125188 A1 | 5/2011 | Goraltchouk et al. |
| 2011/0130774 A1 | 6/2011 | Criscuolo et al. |
| 2011/0166597 A1 | 7/2011 | Herrmann et al. |
| 2011/0264138 A1 | 10/2011 | Avelar et al. |
| 2011/0288583 A1 | 11/2011 | Goraltchouk et al. |
| 2011/0319932 A1 | 12/2011 | Avelar et al. |
| 2012/0053601 A1* | 3/2012 | Yoon ............... A61B 17/0491 606/145 |
| 2012/0101522 A1 | 4/2012 | Megaro et al. |
| 2012/0109188 A1 | 5/2012 | Viola |
| 2013/0072971 A1 | 3/2013 | Kim et al. |
| 2013/0103078 A1 | 4/2013 | Longo et al. |
| 2013/0165971 A1 | 6/2013 | Leung et al. |
| 2013/0172931 A1 | 7/2013 | Gross et al. |
| 2013/0180966 A1 | 7/2013 | Gross et al. |

(56) References Cited

U.S. PATENT DOCUMENTS

| | | | |
|---|---|---|---|
| 2013/0204295 A1 | 8/2013 | Hunter et al. | |
| 2013/0226233 A1 | 8/2013 | D'Agostino et al. | |
| 2013/0226234 A1 | 8/2013 | Avelar et al. | |
| 2013/0238021 A1 | 9/2013 | Gross et al. | |
| 2013/0238022 A1 | 9/2013 | Gross et al. | |
| 2013/0245684 A1 | 9/2013 | Ruff et al. | |
| 2013/0317545 A1 | 11/2013 | Gross et al. | |

FOREIGN PATENT DOCUMENTS

| | | |
|---|---|---|
| CN | 2640420 | 9/2004 |
| DE | 01810800 | 6/1970 |
| DE | 03227984 | 2/1984 |
| DE | 3735649 A1 | 5/1989 |
| DE | 04302895 | 8/1994 |
| DE | 19618891 | 4/1997 |
| DE | 19802213 | 8/1999 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0513736 | 2/1995 |
| EP | 0464479 | 3/1995 |
| EP | 0464480 | 3/1995 |
| EP | 0576337 A1 | 3/1997 |
| EP | 0576337 B1 | 3/1997 |
| EP | 0574707 | 8/1997 |
| EP | 0612504 | 11/1997 |
| EP | 0632999 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 0717958 | 8/2000 |
| EP | 0705567 | 3/2002 |
| EP | 0673624 | 8/2002 |
| EP | 0839499 | 9/2003 |
| EP | 0755656 | 12/2003 |
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 1852071 B1 | 11/2007 |
| EP | 1897500 B1 | 3/2008 |
| EP | 2036502 | 3/2009 |
| EP | 2166957 B1 | 3/2010 |
| EP | 1948261 | 11/2010 |
| EP | 1726317 | 7/2012 |
| FR | 2619129 | 2/1989 |
| FR | 2693108 | 1/1994 |
| GB | 267007 | 3/1927 |
| GB | 1091282 | 11/1967 |
| GB | 1428560 | 7/1973 |
| GB | 1506362 | 4/1978 |
| GB | 1508627 | 4/1978 |
| JP | 1506362 | 4/1978 |
| JP | 54-116419 | 9/1979 |
| JP | 63288146 | 11/1988 |
| JP | 001113091 | 5/1989 |
| JP | 3-165751 | 7/1991 |
| JP | 4-096758 | 3/1992 |
| JP | 4-266749 | 9/1992 |
| JP | 9-103477 | 4/1997 |
| JP | 410085225 | 4/1998 |
| JP | 11-313826 | 11/1999 |
| JP | 011332828 | 12/1999 |
| JP | 2002-059235 | 2/2002 |
| JP | 2003-275217 | 9/2003 |
| JP | 2009-118967 | 6/2009 |
| KR | 10-2005-0072908 A | 7/2005 |
| KR | 6013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 | 1/2006 |
| SU | 1725847 A1 | 4/1992 |
| SU | 1745214 | 7/1992 |
| SU | 1752358 | 8/1992 |
| WO | WO 1996/006565 | 3/1966 |
| WO | WO 1986/000020 | 1/1986 |
| WO | WO 1987/001270 | 3/1987 |
| WO | WO 1988/009157 | 12/1988 |
| WO | WO 1989/005618 | 6/1989 |
| WO | WO 1990/009149 | 8/1990 |
| WO | WO 1990/014795 | 12/1990 |
| WO | WO 1992/022336 | 12/1992 |
| WO | WO 1995/016399 | 6/1995 |
| WO | WO 1995/029637 | 11/1995 |
| WO | WO 1997/000047 | 1/1997 |
| WO | WO 1998/052473 | 11/1998 |
| WO | WO 1998/055031 | 12/1998 |
| WO | WO 1999/021488 | 5/1999 |
| WO | WO 1999/033401 | 7/1999 |
| WO | WO 1999/052478 | 10/1999 |
| WO | WO 1999/059477 | 11/1999 |
| WO | WO 1999/062431 | 12/1999 |
| WO | WO 2000/051658 | 9/2000 |
| WO | WO 2000/051685 | 9/2000 |
| WO | WO 2001/006952 | 2/2001 |
| WO | WO 2001/056626 | 8/2001 |
| WO | WO 2003/001979 | 1/2003 |
| WO | WO 2003/003925 | 1/2003 |
| WO | WO 2003/045255 | 6/2003 |
| WO | WO 2003/077772 | 9/2003 |
| WO | WO 2003/092758 | 11/2003 |
| WO | WO 2003/103733 | 12/2003 |
| WO | WO 2003/103972 | 12/2003 |
| WO | WO 2003/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2007/145614 | 12/2007 |
| WO | WO 2008/128113 | 10/2008 |
| WO | WO 2008/150773 | 12/2008 |
| WO | WO 2008/150773 A1 | 12/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO 2009/151876 | 12/2009 |
| WO | WO 2010/052007 | 5/2010 |
| WO | WO 2011/053375 | 5/2011 |

(56) References Cited

FOREIGN PATENT DOCUMENTS

| WO | WO 2011/090628 | 7/2011 |
|---|---|---|
| WO | WO 2011/139916 | 11/2011 |
| WO | WO 2011/140283 | 11/2011 |
| WO | WO 2011/156733 A3 | 12/2011 |

OTHER PUBLICATIONS

Communication from EPO re: 10000486 dated Apr. 4, 2011, 4 pages.
European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 2, 2007, 2 pages.
European Search Report for EP07016222 dated Jan. 7, 2008.
European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report re: 10004453 dated Jun. 15, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10011872 dated Apr. 20, 2011.
European Search Report for EP10012437 dated Apr. 28, 2011.
European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2007/002688 dated Aug. 14, 2008.
International Preliminary Report re: PCT/US2008/060127 dated Oct. 13, 2009.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2009/044274 dated Nov. 17, 2010.
International Preliminary Report re: PCT/US2011/035431 dated Nov. 6, 2012.
International Preliminary Report re: PCT/US2011/059238 dated May 7, 2013.
International Search Report for PCT/US1994/09631 dated Dec. 9, 1994.
International Search Report for PCT/US1998/10478 dated Sep. 23, 1998.
International Search Report for PCT/US2002/20449 dated May 20, 2003.
International Search Report for PCT/US2002/027525 dated Dec. 9, 2002, 3 pages.
International Search Report for PCT/US2003/030424 dated Nov. 1, 2004.
International Search Report for PCT/US2003/030664 dated May 25, 2004.
International Search Report for PCT/2003/030666 dated Dec. 15, 2004.
International Search Report for PCT/US2003/025088 dated Dec. 29, 2003.
International Search Report re: PCT/US2003/030674 dated Sep. 2, 2004.
International Search Report re: PCT/US2004/014962 dated Feb. 24, 2005.
International Search Report for PCT/US2005/017028 dated Mar. 26, 2008.
International Search Report for PCT/US2007/002688 dated Oct. 22, 2007.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/040545 dated Oct. 29, 2009.
International Search Report for PCT/US2009/063081 dated Aug. 2, 2010.
International Search Report for PCT/US2009/041685 dated Dec. 22, 2009.
International Search Report for PCT/US2009/044274 dated Jan. 15, 2010.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report for PCT/US2011/059238 dated May 21, 2012.
International Search Report for PCT/US2011/060069 dated May 18, 2012.
International Search Report for PCT/US2012/030441 dated Sep. 27, 2012.
International Search Report for PCT/US2012/041001 dated Sep. 26, 2012.
Partial European Search Report re: EP05025816 dated Mar. 20, 2006.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Singapore Search Report for Singapore Patent Application No. 201103117-6 dated Mar. 8, 2013.
Supplementary European Search Report re: EP98923664 dated Jun. 12, 2001.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: EP03785177 dated May 19, 2009.

(56) References Cited

OTHER PUBLICATIONS

Supplementary European Search Report re: 05750101 dated Apr. 7, 2010.
Supplementary European Search Report re: 07017663 dated Nov. 7, 2007.
Written Opinion of the International Searching Authority re: PCT/US2010/056898 dated Aug. 2, 2011.
Written Opinion of the International Searching Authority re: PCT/US2012/041001 dated Sep. 26, 2012.
U.S. Appl. No. 09/943,733, filed Aug. 31,2001.
U.S. Appl. No. 10/065,280, filed Sep. 30, 2002.
U.S. Appl. No. 10/420,993, filed Apr. 22, 2003.
International Preliminary Report on Patentability re: PCT/US2008/064921 dated Dec. 1, 2009.
International Preliminary Report on Patentability re: PCT/US2008/0075849 dated Mar. 16, 2010.
International Preliminary Report on Patentability re: PCT/US2011/040014 dated Dec. 14, 2012.
International Search Report re: PCT/US2008/064921 dated Nov. 19, 2008.
International Search Report re: PCT/US2008/0075849 dated Jun. 23, 2009.
International Search Report re: PCT/US2011/040014 dated Feb. 9, 2012.
Bacci, Pier Antonio, "Chirurgia Estetica Mini Invasiva Con Fili Di Sostegno", Collana di Arti, Pensiero e Scienza; Minelli Editore-2006; 54 pgs.
Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Bellin, I. et al., "Polymeric triple-shape materials", Proceedings of the National Academy of Sciences of the United States of America Nov. 28, 2006; 2103(48):18043-18047.
Boenisch, U.W. et al 'Pull-Out strength and stiffness of meniscal repair using absorbable arrows or Ti-Cron vertical and horizontal loop sutures' American Journal of Sports Medicine, Sep.-Oct. (1999) vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al 'The Suture Repair of One-Millimeter Vessels, microvascular surgery' (1966) Report of First Conference; Oct. 6-7 pp. 24-35.
Bunnell, S. 'Gig pull-out suture for tendons' J Bone Joint Surg. Am (1954) vol. 36A, No. 4 pp. 850-851.
CCPR Centro De Cirurgia Plastica e Reabilitacao 'Up Lifting (Aptos Threads) http://ccpr.com.br/upl-l.htm, Aug. 19, 2002 pp. 1-2.
Dahlin, Lars, "Techniques of Peripheral Nerve Repair", Scandinavian Journal of Surgery 97: 310-316, 2008.
Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.
Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al 'Tissue holding performance of knotless absorbable sutures' Society for Biomaterials 29th Annual Meeting Transactions (2003) p. 101.
Declaration of Dr. Gregory L. Ruff, dated Aug. 19, 2005, 8 pages, with Exhibits A-E.
De Persia, Raúl et al., "Mechanics of Biomaterials: Sutures After the Surgery", Applications of Engineering Mechanics in Medicine, GED-University of Puerto Rico, Mayaguez May 2005, p. F1-F27.
Delorenzi, C.L., "Barbed Sutures: Rationale and Technique", Aesthetic Surg. J. Mar. 26, 2006(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times 2006 Feb. 27(2): 2 pages.
Gross, R.A. et al 'Biodegradable Polymers for the Environment' Science (2002) vol. 297, Issue 5582 pp. 803.
Han, H. et al 'Mating and Piercing Micromechanical Suture for Surface Bonding Applications' (1991) Proceedings of the 1991 Micro Electro Mechanical Systems (MEMS>91), An Investigation of Micro Structures, Sensors, Actuators, Machines and Robots pp. 253-258.
Ingle, N. P. et al 'Barbed Suture Anchoring Strength: Applicability to Dissimilar Polymeric Materials' College of Textiles, North Carolina State University, 7th World Biomaterials Congress 2004, 1 page.
Ingle, N. P. et al 'Mechanical Performance and Finite Element Analysis of Bi-directional Barbed Sutures' Master of Science in Textile Technology & Management at North Carolina State University Aug. 2003, 126 pages.
Ingle, N. P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, The Next Generation Oct. 17-19 2005, New Jersey Institute of Technology, Newark, NJ, 4 pages.
Jennings et al 'A New Technique in primary tendon repair' Surg. Gynecol. Obstet. (1952) vol. 95, No. 5 pp. 597-600.
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio[($\in$-hydroxycaproate)-co-glycolate]dimethacrylates and Butyl Acrylate with Adjustable Hydrolytic Degradation Rate", Biomacromolecules 2007;8(3):1018-1027.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendlein, A. et al 'Biodegradable, Elastic Shape-Memory Polymers for Potential Biomedical Applications' (2002) Science vol. 296 pp. 1673-1676.
Lendlein, A. et al 'Shape-Memory Polymers' Agnew Chem. Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures' International Conference & Exhibition on Healthcare & Medical Textiles, Jul. 8-9 2003 pp. 1-8.
Leung, J. et al 'Barbed, Bi-directional Surgical Sutures: In Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Leung, J. et al 'Performance Enhancement of a Knotless Suture via Barb Geometry Modifications' 7th World Biomaterials Congress 2004, 1 page.
Li, Y.Y. et al 'Polymer Replicas of Photonic Porous Silicon for Sensing and Drug Delivery Applications' (2003) Science vol. 299 pp. 2045-2047
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.

(56) References Cited

OTHER PUBLICATIONS

Madduri, Srinivas, et al., "Neurotrophic factors release from nerve conduits for peripheral axonal regeneration", European Cells and Materials vol. 16; Suppl. 1 (2008), p. 14.
Madhave et al 'A biodegradable and biocompatible gecko-inspired tissue adhesive' PNAS 105(7) pp. 2307-2312 (2008).
Maitland et al., "Prototype laser-activated shape memory polymer foam device for embolic treatment of aneurysms", Journal of Biomedical Optics 2007 May/Jun.;12(3): pp. 030504-1 to 030504-3.
Malina, M. et al 'Endovascular AAA Exclusion: Will Stents with Hooks and Barbs Prevent Stent-Graft Migration' Journal Endovascular Surgery (1998) vol. 5 pp. 310-317.
Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.
Martin, D.P. et al 'Medical applications of poly-4-hydroxybutyrate: a strong flexible absorbable biomaterial' Biochemical Engineering Journal vol. 16 (2003) pp. 97-105.
Mason, M.L. 'Primary and Secondary Tendon Suture. A discussion of the significance of technique in tendon surgery' (1940) Surg Gynecol Obstet 70.
McKee, GK 'Metal anastomosis tubes in tendon suture' The Lancet (1945) pp. 659-660.
McKenzie 'An Experimental Multiple Barbed Suture for the Long Flexor Tendons of the Palm and Fingers' The Journal of Bone and Joint Surgery (1967) vol. 49B, No. 3 pp. 440-447.
Middleton and Tipton 'Synthetic Biodegradable Polymers as Medical Devices' (1998) Medical Plastics and Biomaterials Magazine, 9 pages.
Moran et al., "Bidirectional-Barbed Sutured Knotless Running Anastomosis v Classic van Velthovan in a Model System", Journal of Endourology Oct. 2007; 21(10); 1175-1177.
Mullner, "Metal Foam Has a Good Memory", Dec. 18, 2007 Original story at <http://www.physorg.com/news117214996.html>.
Murtha et al., "Evaluation of a Novel Technique for Wound Closure Using A Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D., "Bidirectional Barbed Sutures for Wound Closure: Evolution and Applications", Journal of the American College of Certified Wound Specialists (2009) 1, 51-57.
Paul, Malcolm D. and Rui Avelar, "Quill™ SRS Techniques & Procedures A Novel Approach to Soft Tissue Approximation", Canada, Angiotech Pharmaceuticals, Inc., First Edition Aug. 2007: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Second Edition Aug. 2008: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Third Edition 2009, 8 2007-2009: 27 pages.
Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, 8 2007-2010: 27 pages.
Paul, Malcolm D., "Using Barbed Sutures in Open/Subperiosteal Midface Lifting", Aesthetic Surgery Journal 2006(26): 725-732.
Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.
Quill Medical, Inc. 'Quill Medical's Novel-Self-Anchoring Surgical Suture Approved for Sale in Europe' Press Release; Research Triangle Park, N. C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N. C., Nov. 4, 2004, 1 page.
Richert, Ludovic, et al., "Surface Nanopatterning to Control Cell Growth", Advanced Materials 2008(15): 1-5.
Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects-Influence of suture numbers and reconstruction of nerve bifurcations", Restorative Neurology and Neuroscience 23 (2005) 79-85.
Schmid A. et al 'The outspreading anchor cord. A material for arthroscopic suturing of a fresh anterior cruciate ligament rupture' Surgical Clinic of the University of Gottingen (1987) pp. 417-426.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Clin Plastic Surg 36 (2009); pp. 281-306.
Sulamanidze, M.A. et al 'Clinical aspects of bloodless facelift using APTOS filaments' A.V. Vishnevsky Institute of Surgery, Bol'shaya Serpukhovskaya ul, 7, 113811, Moscow, Russia (2002) pp. 24-34.
Sulamanidze, M.A. et al 'Facial lifting with Aptos threads' International Journal of Cosmetic Surgery and Aesthetic Dermatology (2001) No. 4 pp. 1-8.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 19-26.
Sulamanidze, M.A. et al 'Removal of Facial Soft Tissue Ptosis with Special Threads' Dermatol Surg (2002) vol. 28 pp. 367-371.
Sulamanidze, MD, M.A., et al., "Soft tissue lifting in the mid-face: old philosophy, new approach-internal stitching technique (APTOS Needle)", Plastic and Aesthetic Surgery Clinic Total Sharm, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Tan E.L. et al., "A wireless, passive strain sensor based on the harmonic response of magnetically soft materials", Smart Materials and Structures 17 (2008): pp. 1-6.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.

(56) References Cited

OTHER PUBLICATIONS

Australian Office Action, Patent Examination Report No. 1, dated Feb. 8, 2016 for Application No. AU 2015201140, 3 pgs.
Australian Office Action, Patent Examination Report No. 1, dated Sep. 27, 2013 for Application No. AU 2011265232, 3 pgs.
Canadian Office Action dated May 31, 2017 for Application No. CA 2,801,271, 4 pgs.
Chinese Office Action, First Office Action, and Search Report dated Oct. 23, 2014 for Application No. CN 201180028805.1, 8 pgs.
European Supplemental Partial Search Report and Written Opinion dated Oct. 13, 2015 for Application No. EP 11793252.5, 7 pgs.
European Search Report and Written Opinion dated Jul. 10, 2017 for Application No. EP 16201158.9, 11 pgs.
European Search Report, Partial, dated Mar. 20, 2017 for Application No. EP 16201158.9, 6 pgs.
Japanese Office Action, Notification of Reasons for Refusal, dated Feb. 3, 2015 for Application No. JP 2013-514393, 3 pgs.
Japanese Office Action, Notification of Reasons for Refusal, dated Jul. 7, 2015 for Application No. JP 2013-514393, 4 pgs.
Mexican Office Action dated Jun. 8, 2015 for Application No. MX/a/2012/014456, 4 pgs.
Russian Office Action dated Apr. 9, 2015 for Application No. RU 2012157810/14(091057), 6 pgs.

\* cited by examiner

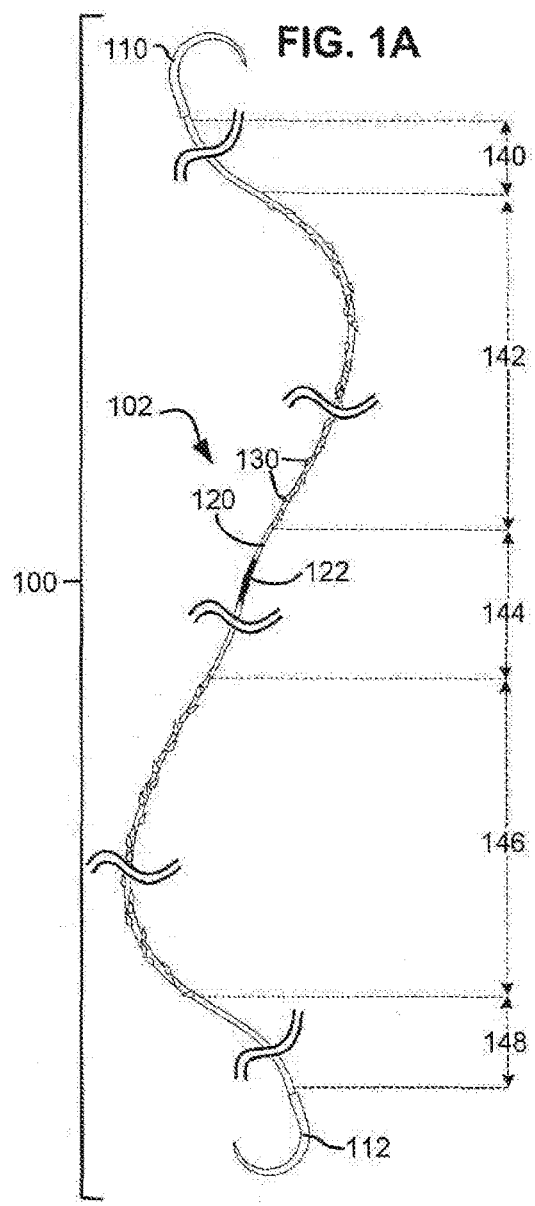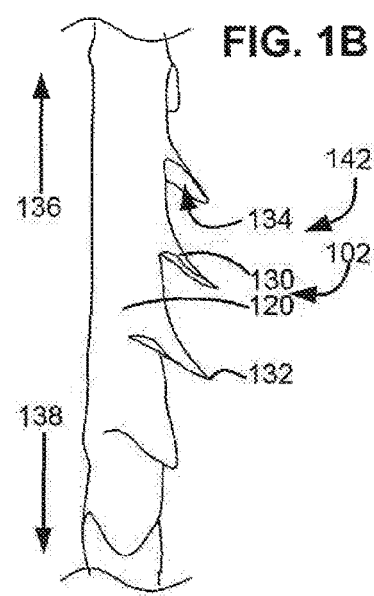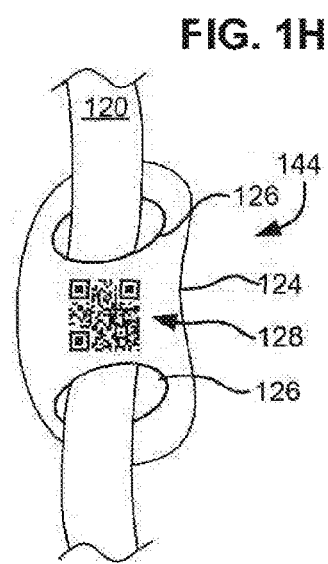

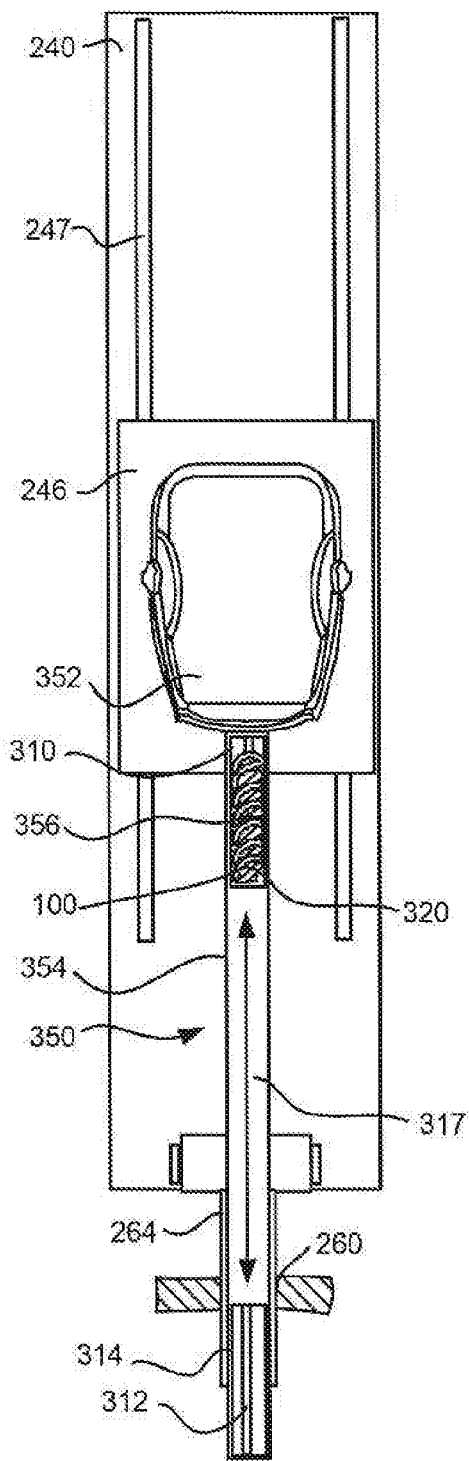
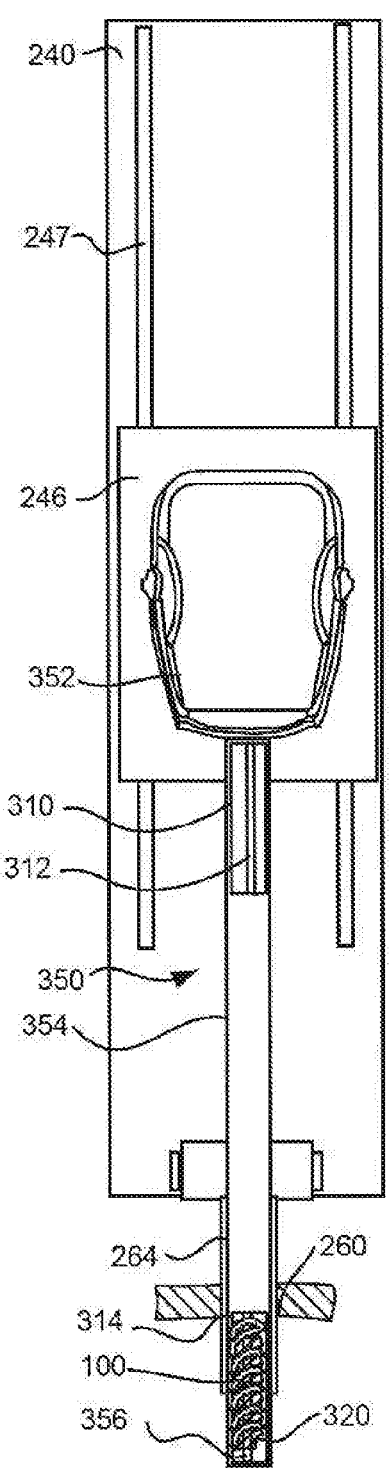

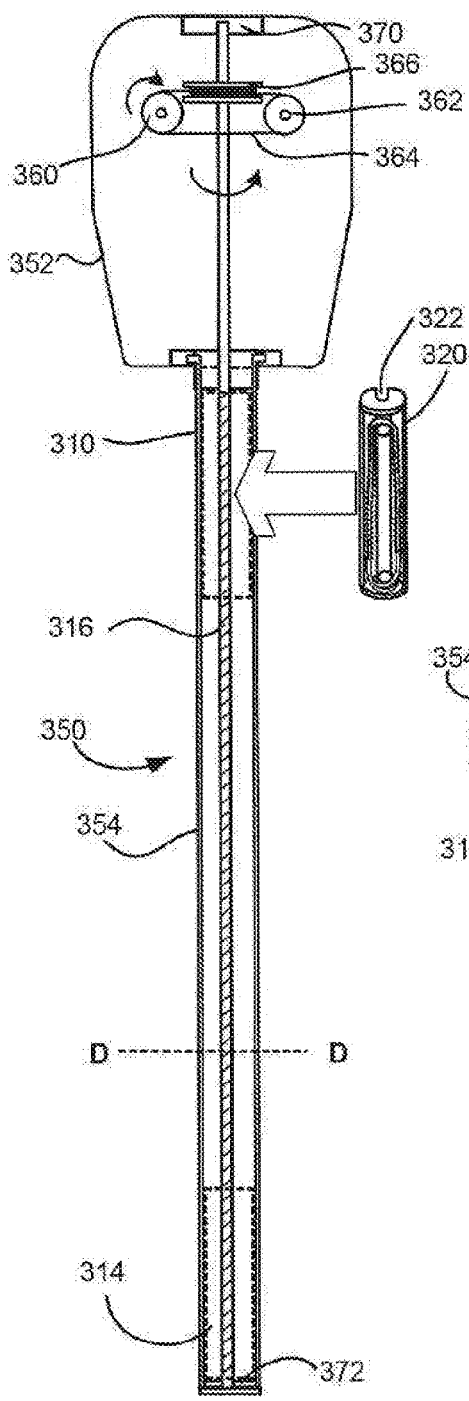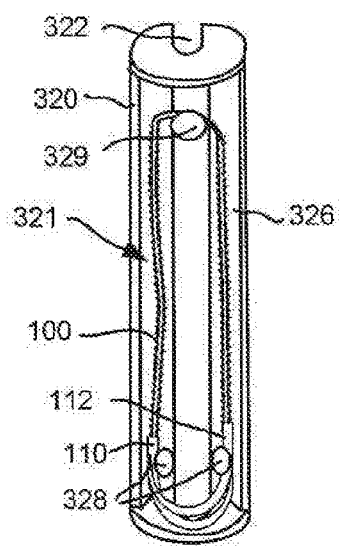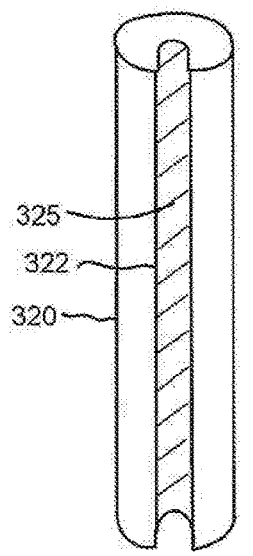

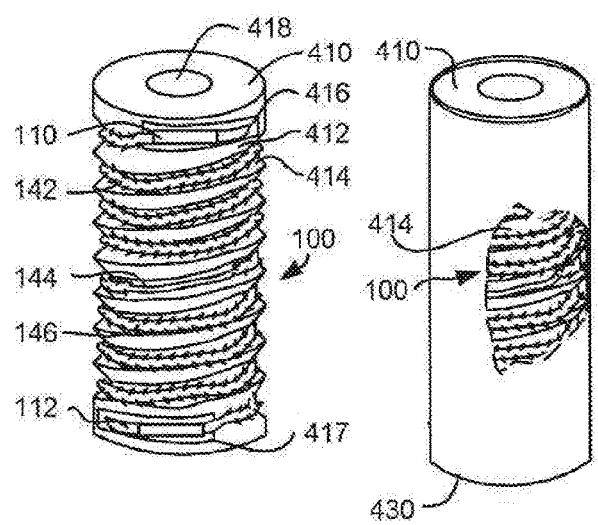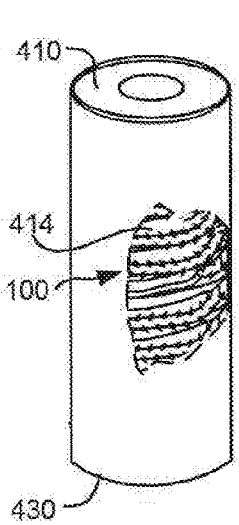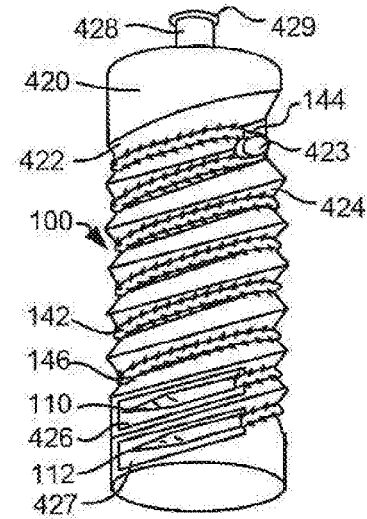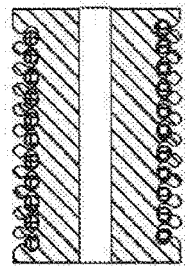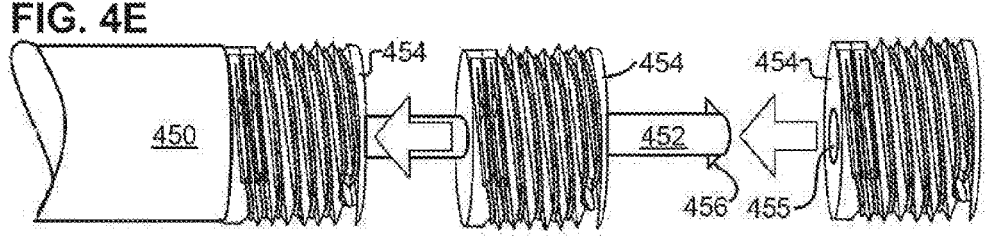

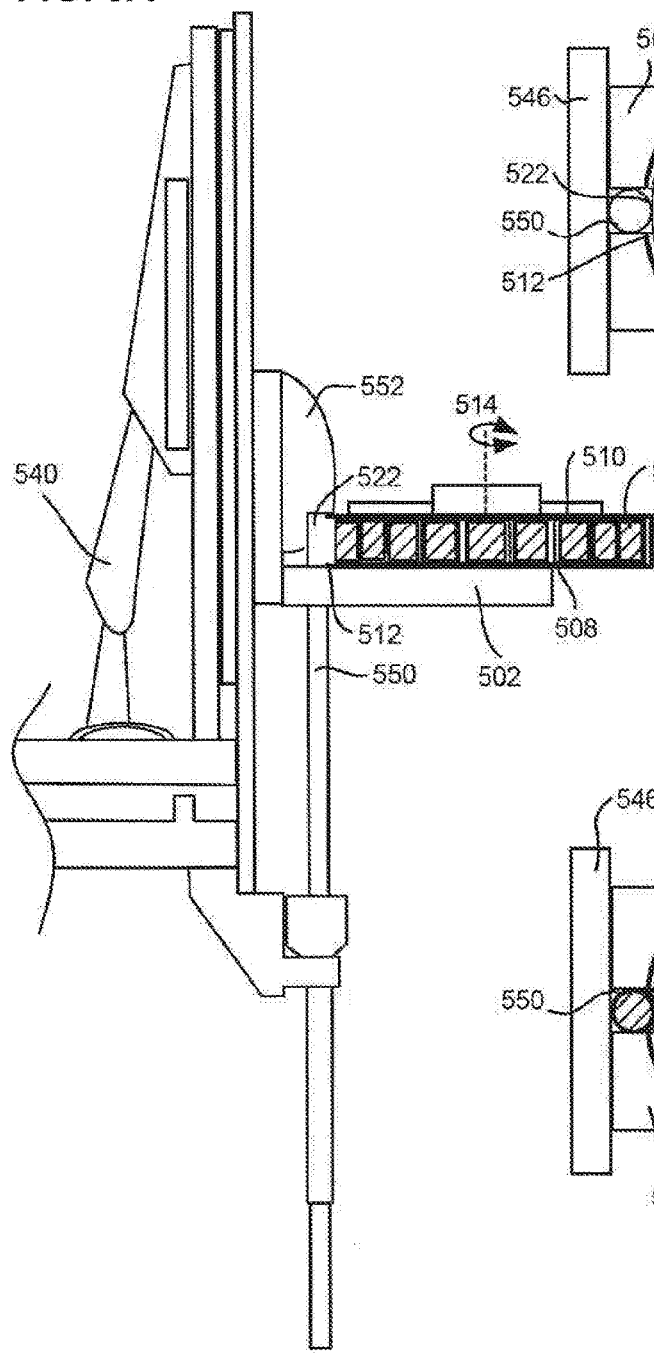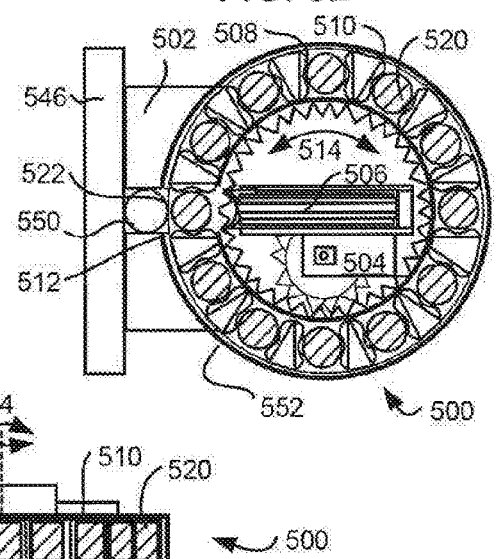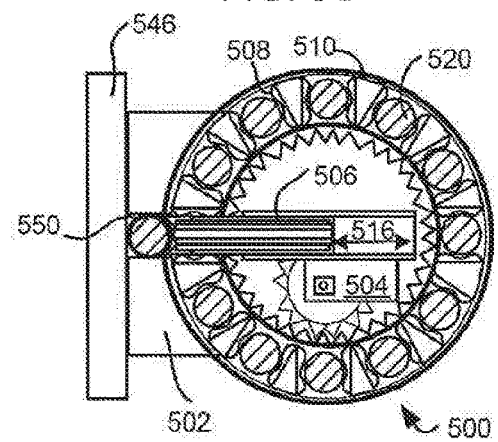

SUTURE DELIVERY TOOLS FOR ENDOSCOPIC AND ROBOT-ASSISTED SURGERY AND METHODS

CROSS-REFERENCE TO RELATED APPLICATIONS

This application is a National Stage Application of international application PCT/US2011/040014, filed Jun. 10, 2011, which claims the benefit U.S. Provisional Application No. 61/354,009, filed Jun. 11, 2010, which application is herein incorporated by reference in its entirety.

FIELD OF INVENTION

The present invention relates to systems for packaging, selecting and delivering sutures to surgical sites within a patient during surgical procedures including minimally-invasive surgical procedures.

BACKGROUND OF INVENTION

Minimally invasive surgery (MIS) procedures avoid open invasive surgery in favor of closed or local surgery with less trauma. Minimally invasive surgical procedures typically involve remote manipulation of instruments with indirect observation of the surgical field through an endoscope or similar device, and are carried out through a small access port through the skin or through a body cavity or anatomical opening. Minimally invasive medical techniques thereby reduce tissue damage during diagnostic or surgical procedures, thereby reducing patient recovery time, discomfort, and deleterious side effects. Minimally invasive medical techniques consequently shorten the average length of a hospital stay for a procedure when compared to standard open surgery.

One form of minimally invasive surgery is endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide access ports for laparoscopic surgical instruments. The laparoscopic surgical instruments generally include an endoscope for visualizing the surgical field and specialized surgical instruments which is, in some embodiments, passed through the access ports. The instruments can include clamps, graspers, scissors, staplers, and needle holders, for example. The surgical instruments may or may not be similar to those used in conventional (open) surgery; typically that the working end of each instrument is separated from its handle by an elongated shaft and is sized and configured to fit through the access port. To perform surgical procedures, the surgeon passes the surgical instruments through the access ports to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, thoracoscopy, retroperitoneoscopy, pelviscopy, nephroscopy, cystoscopy, cisternoscopy, sinoscopy, hysteroscopy, urethroscopy, craniotomy, and natural orifice surgery (for example of the airway and gastrointestinal tract).

There are many disadvantages relating to MIS technology utilizing hand-operated instruments. For example, existing MIS instruments deny the surgeon the flexibility of instrument placement found in open surgery. Most current laparoscopic instruments have rigid shafts, so that it can be difficult to approach the surgical site through the small incision. Additionally, the length and construction of many endoscopic instruments reduces the surgeon's ability to feel forces exerted by the instrument on tissues and organs at the surgical site. The lack of dexterity and sensitivity of endoscopic instruments is an impediment to the expansion of minimally invasive surgery.

Minimally invasive telesurgery systems have been developed to increase a surgeon's dexterity when working within an internal surgical site, as well as to allow a surgeon to operate on a patient from a remote location. In a telesurgery system, the surgeon is provided with an image of the surgical site as with endoscopy. However, rather than manipulating the surgical instruments directly, the surgeon performs the surgical procedures on the patient by manipulating master input or control devices at a console. The master input and control devices control the motion of surgical instruments utilizing telemanipulators. Depending on the system, telesurgery systems may overcome some but not all of the lack of dexterity and sensitivity of endoscopic instruments. Surgical telemanipulator systems are often referred to as robotic or robotically-assisted surgery systems.

Many MIS procedures including MIS telesurgery procedures employ wound closure devices such as sutures, staples and tacks for closing wounds, repairing traumatic injuries or defects, joining tissues together (bringing severed tissues into approximation, closing an anatomical space, affixing single or multiple tissue layers together, creating an anastomosis between two hollow/luminal structures, adjoining tissues, attaching or reattaching tissues to their proper anatomical location), attaching foreign elements to tissues (affixing medical implants, devices, prostheses and other functional or supportive devices), and for repositioning tissues to new anatomical locations (repairs, tissue elevations, tissue grafting and related procedures) to name but a few examples. Sutures typically consist of a filamentous suture thread attached to a needle with a sharp point. Suture threads can be made from a wide variety of materials including bioabsorbable (i.e., that break down completely in the body over time), or non-absorbable (permanent; non-degradable) materials. Absorbable sutures have been found to be particularly useful in situations where suture removal might jeopardize the repair or where the natural healing process renders the support provided by the suture material unnecessary after wound healing has been completed; as in, for example, completing an uncomplicated skin closure. Non-degradable (non-absorbable) sutures are used in wounds where healing is, in some embodiments, expected to be protracted or where the suture material is needed to provide physical support to the wound for long periods of time; as in, for example, deep tissue repairs, high tension wounds, many orthopedic repairs and some types of surgical anastomosis. Also, a wide variety of surgical needles are available, and the shape, and size of the needle body and the configuration of the needle tip is typically selected based upon the needs of the particular application.

To use an ordinary suture, the suture needle is advanced through the desired tissue on one side of the wound and then through the adjacent side of the wound. The suture is then formed into a "loop" which is completed by tying a knot in the suture to hold the wound closed. Knot tying takes time and causes a range of complications, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops associated with knot tying may lead to ischemia (knots can create tension points that can strangulate tissue and limit blood flow to the region) and increased risk of dehiscence or rupture at the surgical wound. Knot tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time). The time taken by suture tying and the range of complications is exasperated by the lack of dexterity and sensitivity of MIS instruments.

Self-retaining sutures (including barbed sutures) differ from conventional sutures in that self-retaining sutures possess numerous tissue retainers (such as barbs) which anchor the self-retaining suture into the tissue following deployment and resist movement of the suture in a direction opposite to that in which the retainers face, thereby eliminating the need to tie knots to affix adjacent tissues together (a "knotless" closure). This facilitates and expedites deployment of self-retaining sutures compared to ordinary sutures. Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatus for forming barbs on sutures have been described in, for example, U.S. Pat. No. 6,848,152. It is noted that all patents, patent applications and patent publications identified throughout are incorporated herein by reference in their entirety. Self-retaining sutures result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots —through the surface of the skin. All of these features are thought to reduce scarring, improve cosmesis, and increase wound strength relative to wound closures using plain sutures or staples. Thus, self-retaining sutures, because such sutures avoid knot tying, allow patients to experience an improved clinical outcome, and also save time and costs associated with extended surgeries and follow-up treatments.

SUMMARY OF INVENTION

The present invention is generally directed to surgical instruments for delivering sutures and in particular self-retaining sutures to a surgical site in an MIS procedure including a robot-assisted MIS procedures. Despite the multitude of advantages of unidirectional and bidirectional self-retaining sutures for MIS and telesurgical MIS, there remains a need to improve upon the design of the suture such that the functionality is enhanced and/or additional functionality is provided. The present invention overcomes the problems and disadvantages of the prior art by providing packages and systems for delivering self-retaining sutures to the surgical site. The self-retaining sutures can be deployed by endoscopic and/or telesurgical instruments at the surgical site for suturing, approximating and holding tissue. The self-retaining sutures provide advantages which compensate for lack of dexterity and sensitivity present in instruments used MIS and telesurgical MIS procedures. In this way, the time taken for the procedure is reduced and the clinical outcome is enhanced.

In accordance with an aspect of the present invention, a method of performing MIS procedure in a body cavity of a patient includes providing a suture package containing a suture or self-retaining suture and introducing the package to an operative site within a patient for use during an MIS procedure. The suture or self-retaining suture is then manipulated by the MIS instrument to suture, approximate and/or hold tissue.

In some embodiments, the suture package is introduced into the cavity using a telesurgical suture delivery instrument. The suture delivery instrument delivers suture to the cavity under the control of the surgeon and positions the suture such that it is, in some embodiments, located by the surgeon and manipulated using MIS instruments.

In some embodiments, the suture package is introduced into the cavity using a telesurgical suture delivery system. The telesurgical suture delivery system delivers suture to the cavity using a telemanipulator under the control of the surgeon and positions the suture such that it is, in some embodiments, located by the surgeon and manipulated by MIS instruments.

In some embodiments, the suture package includes a spool for the suture and self-retaining suture. The spool releasably secures one or more self-retaining sutures and surgical needles therein.

In a specific embodiment, a cartridge releasably secures one or more sutures. A cartridge is selected and attached to the suture delivery system which delivers the cartridge and suture to the surgical site. In some embodiments, a variety of different cartridges is available having different sutures.

In a specific embodiment, a cartridge releasably secures one or more sutures. A cartridge is selected and attached to the suture delivery system which delivers the cartridge and suture to the surgical site.

In some embodiments, different cartridges are available having different sutures the cartridges have features which allow them to be identified and/or selected by an automated delivery system responsive to instructions from a surgeon.

In some embodiments, suture cartridges provided with visible and/or machine readable markings, codes, tags or the like which are indicative of one or more properties of a suture loaded in the cartridge.

The details of one or more embodiments are set forth in the description below, including the embodiments identified in paragraphs 124 to 195. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

Features of the invention, its nature and various advantages will be apparent from the accompanying drawings and the following detailed description of various embodiments.

FIG. 1A shows a perspective view of a bidirectional self-retaining suture in accordance with an embodiment of the present invention.

FIG. 1B shows an enlarged views of a portion of the bidirectional suture of FIG. 1A.

FIG. 1H includes a portion of the suture of FIG. 1A also including an optional pledget.

FIGS. 3A and 3B show suture cartridge delivery utilizing an alternative suture delivery tool according to an embodiment of the present invention.

FIGS. 3C and 3D show internal and sectional views, respectively, of the suture delivery tool of FIGS. 3A and 3B.

FIGS. 3E and 3F show different views of a suture delivery cartridge suitable for use with the suture delivery tool of FIGS. 3A through 3D according to an embodiment of the present invention.

FIGS. 4A to 4H show suture cartridges according to embodiments of the present invention.

FIGS. 5A to 5C show a suture cartridge magazine according to an embodiment of the present invention.

DETAILED DESCRIPTION

Definitions

Figure 1C:
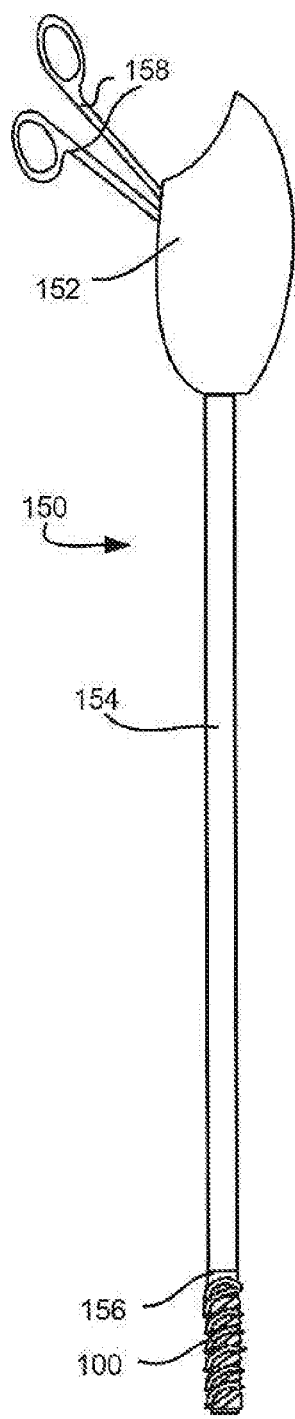
FIG. 1C shows a view of a suture delivery instrument according to an embodiment of the present invention.

Definitions of certain terms that is, in some embodiments, used hereinafter include the following.

"Self-retaining system" refers to a self-retaining suture together with devices for deploying the suture into tissue. Such deployment devices include, without limitation, suture needles and other deployment devices as well as sufficiently rigid and sharp ends on the suture itself to penetrate tissue.

"Self-retaining suture" refers to a suture that comprises features on the suture filament for engaging tissue without the need for a knot or suture anchor. S elf-retaining sutures as described herein are produced by any suitable method, including without limitation, injection molding, stamping, cutting, laser, extrusion, and so forth. With respect to cutting, polymeric thread or filaments is, in some embodiments, manufactured or purchased for the suture body, and the retainers can be subsequently cut onto the suture body; the retainers are, in some embodiments, hand-cut, laser-cut, or mechanically machine-cut using blades, cutting wheels, grinding wheels, and so forth. During cutting either the cutting device or the suture thread is, in some embodiments, moved relative to the other, or both is, in some embodiments, moved, to control the size, shape and depth of cut 210. Particular methods for cutting barbs on a filament are described in U.S. patent application Ser. No. 09/943,733 titled "Method Of Forming Barbs On A Suture And Apparatus For Performing Same" to Genova et al., now U.S. Pat. No. 6,848,152, issued on Feb. 1, 2005, and U.S. patent application Ser. No. 10/065,280 titled "Barbed Sutures" to Leung et al., now U.S. Pat. No. 8,795,332, issued on Aug. 5, 2014, both of which are incorporated herein by reference.

"Tissue retainer" (or simply "retainer") refers to a physical feature of a suture filament which is adapted to mechanically engage tissue and resist movement of the suture in at least one axial directions. By way of example only, tissue retainer or retainers can include hooks, projections, barbs, darts, extensions, bulges, anchors, protuberances, spurs, bumps, points, cogs, tissue engagers, traction devices, surface roughness, surface irregularities, surface defects, edges, facets and the like. In certain configurations, tissue retainers are adapted to engage tissue to resist movement of the suture in a direction other than the direction in which the suture is deployed into the tissue by the physician, by being oriented to substantially face the deployment direction. In some embodiments, the retainers lie flat when pulled in the deployment direction and open or "fan out" when pulled in a direction contrary to the deployment direction. As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from the deployment position (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self-retaining suture in place. In certain other embodiments, the tissue retainers is, in some embodiments, configured to permit motion of the suture in one direction and resist movement of the suture in another direction without fanning out or deploying. In certain other configurations, the tissue retainer is, in some embodiments, configured or combined with other tissue retainers to resist motion of the suture filament in both directions. Typically a suture having such retainers is deployed through a device such as a cannula which prevents contact between the retainers and the tissue until the suture is in the desired location. In some embodiments, mechanical retainers are replaced and/or augmented with chemical and/or adhesive retainers which engage tissue by adhering or physically and/or chemically bonding the suture to surrounding tissue.

"Retainer configurations" refers to configurations of tissue retainers and can include features such as size, shape, flexibility, surface characteristics, and so forth. These are sometimes also referred to as "barb configurations".

"Retainer distribution" refers to the arrangement of retainers on the surface of a filament and can include variables such as orientation, pattern, pitch, and spirality angle.

"Bidirectional suture" refers to a self-retaining suture having retainers oriented in one direction at one end and retainers oriented in the other direction at the other end. A bidirectional suture is typically armed with a needle at each end of the suture thread. Many bidirectional sutures have a transition segment located between the two barb orientations.

"Transition segment" refers to a retainer-free (barb-free) portion of a bidirectional suture located between a first set of retainers (barbs) oriented in one direction and a second set of retainers (barbs) oriented in another direction. The transition segment can be at about the midpoint of the self-retaining suture, or closer to one end of the self-retaining suture to form an asymmetrical self-retaining suture system.

"Suture thread" refers to the filamentary body component of the suture. The suture thread is, in some embodiments, a monofilament, or comprise multiple filaments as in a braided suture. The suture thread is, in some embodiments, made of any suitable biocompatible material, and is, in some embodiments, further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

"Monofilament suture" refers to a suture comprising a monofilamentary suture thread.

"Braided suture" refers to a suture comprising a multifilamentary suture thread. The filaments in such suture threads are typically braided, twisted, or woven together.

"Degradable suture" (also referred to as "biodegradable suture" or "absorbable suture") refers to a suture which, after introduction into a tissue is broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination of these) or by a thermal or photolytic process. Polymer degradation is, in some embodiments, characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). A dissolvable suture can also include partially deacetylated polyvinyl alcohol. Polymers suitable for use in degradable sutures can be linear polymers, branched polymers or multi-axial polymers. Examples of multi-axial polymers used in sutures are described in U.S. Patent Application Publication No. 2002/0161168, U.S. Patent Application Publication No. 2004/0024169, now U.S. Pat. No. 7,026,437, issued on Apr. 11, 2006, and U.S. Patent Application Publication No. 2004/0116620, now U.S. Pat. No. 7,070,858, issued on Jul. 4, 2006. Sutures made from degradable suture material lose tensile strength as the material degrades. Degradable sutures can be in either a braided multifilament form or a monofilament form.

"Non-degradable suture" (also referred to as "non-absorbable suture") refers to a suture comprising material that is not degraded by chain scission such as chemical reaction processes (e.g., hydrolysis, oxidation/reduction, enzymatic mechanisms or a combination of these) or by a thermal or photolytic process. Non-degradable suture material includes polyamide (also known as nylon, such as nylon 6 and nylon 6,6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

"Suture diameter" refers to the diameter of the body of the suture. It is to be understood that a variety of suture lengths is, in some embodiments, used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures is, in some embodiments, more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Needle attachment" refers to the attachment of a needle to a suture requiring same for deployment into tissue, and can include methods such as crimping, swaging, using adhesives, and so forth. The suture thread is attached to the suture needle using methods such as crimping, swaging and adhesives. Attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. US 2004/0088003). The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging or other methods whereby the suture material is inserted into a channel at the blunt end of the needle which is then deformed to a final shape to hold the suture and needle together. As such, atraumatic needles do not require extra time on site for threading and the suture end at the needle attachment site is generally smaller than the needle body. In the traumatic needle, the thread comes out of the needle's hole on both sides and often the suture rips the tissues to a certain extent as it passes through. Most modern sutures are swaged atraumatic needles. Atraumatic needles is, in some embodiments, permanently swaged to the suture or is, in some embodiments, designed to come off the suture with a sharp straight tug. These "pop-offs" are commonly used for interrupted sutures, where each suture is only passed once and then tied. For barbed sutures that are uninterrupted, these atraumatic needles are preferred.

Suture needles may also be classified according to the geometry of the tip or point of the needle. For example, needles is, in some embodiments, (i) "tapered" whereby the needle body is round and tapers smoothly to a point; (ii) "cutting" whereby the needle body is triangular and has a sharpened cutting edge on the inside; (iii) "reverse cutting" whereby the cutting edge is on the outside; (iv) "trocar point" or "taper cut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030 (Mani, Inc., Japan); and U.S. Pat. No. 5,464,422 (W.L. Gore, Newark, Del.); and U.S. Pat. Nos. 5,941,899; 5,425,746; 5,306,288 and 5,156,615 (US Surgical Corp., Norwalk, Conn.); and U.S. Pat. No. 5,312,422 (Linvatec Corp., Largo, Fla.); and U.S. Pat. No. 7,063,716 (Tyco Healthcare, North Haven, Conn.). Other suturing needles are described, for example, in U.S. Pat. Nos. U.S. Pat. Nos. 6,129,741; 5,897,572; 5,676,675; and 5,693,072. The sutures described herein is, in some embodiments, deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Needle diameter" refers to the diameter of a suture deployment needle at the widest point of that needle. While the term "diameter" is often associated with a circular periphery, it can be understood herein to indicate a cross-sectional dimension associated with a periphery of any shape.

"Armed suture" refers to a suture having a suture needle on at least one suture deployment end. "Suture deployment end" refers to an end of the suture to be deployed into tissue; one or both ends of the suture is, in some embodiments, suture deployment ends. The suture deployment end is, in some embodiments, attached to a deployment device such as a suture needle, or is, in some embodiments, sufficiently sharp and rigid to penetrate tissue on its own.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound is, in some embodiments, caused by an act, such as a puncture, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

"Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects and loss of tissue volume effect downward migration of tissue, and fat descends into the plane between the superficial and deep facial fascia, thus causing facial tissue to sag. Face-lift procedures are designed to lift these sagging tissues, and are one example of a more general class of medical procedure known as a tissue elevation procedure. More generally, a tissue elevation procedure reverses the appearance change that results from effects of aging and gravity over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Medical device" or "implant" refers to any object placed in the body for the purpose of restoring physiological function, reducing/alleviating symptoms associated with disease, and/or repairing and/or replacing damaged or diseased organs and tissues. While normally composed of biologically compatible synthetic materials (e.g., medical-grade stainless steel, titanium and other metals or polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

Suture Delivery for Minimally-Invasive Surgery

As discussed above, the present invention provides compositions, configurations, methods of manufacturing and methods of utilizing self-retaining sutures. The invention overcomes the problems and disadvantages of the prior art by delivering self-retaining sutures to the surgical site. The self-retaining sutures can be manipulated by endoscopic and/or robotically-assisted surgical instruments at the site for suturing, approximating and holding tissue. A number of devices have been proposed for delivery surgical elements and accessories for use in MIS procedures. Devices are disclosed, for example, in U.S. Pat. No. 6,986,780 titled "Surgical Element Delivery System And Method" to Rudnick et al. and U.S. Pat. No. 7,125,403 titled "in Vivo Accessories For Minimally Invasive Robotic Surgery" to Julian et al., both or which are incorporated herein by reference in their entirety.

Endoscopic Suture Delivery System

A self-retaining suture is, in some embodiments, unidirectional, having one or more retainers oriented in one direction along the length of the suture thread; or bidirectional, typically having one or more retainers oriented in one direction along a portion of the thread, followed by one or more retainers oriented in another (often opposite) direction over a different portion of the thread (as described with barbed retainers in U.S. Pat. Nos. 5,931,855 and. 6,241,747). Although any number of sequential or intermittent configurations of retainers are possible, a common form of bidirectional self-retaining suture involves a needle at one end of a suture thread which has barbs having tips projecting "away" from the needle until the transition point (often the midpoint) of the suture is reached; at the transition point the configuration of barbs reverses itself about 180° (such that the barbs are now facing in the opposite direction) along the remaining length of the suture thread before attaching to a second needle at the opposite end (with the result that the barbs on this portion of the suture also have tips projecting "away" from the nearest needle). Projecting "away" from the needle means that the tip of the barb is further away from the needle and the portion of suture comprising the barb is, in some embodiments, pulled more easily through tissue in the direction of the needle than in the opposite direction. Put another way, the barbs on both "halves" of a typical bidirectional self-retaining suture have tips that point towards the middle, with a transition segment (lacking barbs) interspersed between them, and with a needle attached to either end.

FIG. 1A illustrates a self-retaining suture system 100. Self-retaining suture system 100 comprises needles 110, 112 attached to self-retaining suture thread 102. Self-retaining suture thread 102 includes a plurality of retainers 130 distributed on the surface of a filament 120. In lead-in section 140 of filament 120 there are no retainers 130. In section 142 of filament 120, there are a plurality of retainers 130 arranged such that the suture can be deployed in the direction of needle 110, but resists movement in the direction of needle 112. In transition section 144, there are no retainers 130. Transition section 122 is, in some embodiments, provided with a marker to facilitate location of the transition section. Transition section 122, as shown, is provided with a visible band 122 to help identify the transition section. Markers are in some embodiments also provided on sections 142, 146 and/or needles 110, 112 in order to help identify the retainer location and orientation of a particular portion of self-retaining suture system 100. In section 146, there is a plurality of retainers 130 arranged such that the suture can be deployed in the direction of needle 112, but resists movement in the direction of needle 110. The retainers 130 in section 146 are larger than the retainers 130 in section 142. The larger retainers are better suited for gripping tissue that is softer and/or less dense than the smaller retainers. In lead-in section 148 of filament 120 there are no retainers 130.

A break is shown in each of sections 140, 142, 144, 146 and 148 to indicate that the length of each section is, in some embodiments, varied and selected depending upon the application for which the suture is intended to be used. For example, transition section 144 can be asymmetrically located closer to needle 110 or needle 112, if desired. A self-retaining suture having an asymmetrically located transition section 144 is, in some embodiments, favored by a physician that prefers to use his dominant hand in techniques that require suturing in opposite directions along a wound. The physician may start further from one end of the wound than the other and stitch the longer portion of the wound with the needle that is located further from the transition section 144. This allows a physician to use his dominant hand to stitch the majority of the wound with the longer arm of the suture. The longer arm of the suture is that section of suture between the transition section and the needle which is located further from the transition section.

FIG. 1B illustrates a magnified view of self-retaining suture thread 102 in section 142. As shown in FIG. 1B, a plurality of retainers 130 is distributed on the surface of filament 120. The affixation of self-retaining sutures after deployment in tissue entails the penetration of retainer ends 132 into the surrounding tissue resulting in tissue being caught between the retainer 130 and the body of suture filament 120. The inner surface 134 of the retainer 130 that is in contact with the tissue that is caught between the retainer 130 and the body of filament 120, is referred to herein as the "tissue engagement surface" or "inner retainer surface." As illustrated in FIG. 1B, each retainer 130 has a tip 132 and tissue retainer surface 134. When self-retaining suture thread 102 is moved in the direction of arrow 136, retainers 130 lies flat against the body of filament 120. However, when self-retaining suture thread 102 is moved in the direction of arrow 138, tip 132 of retainer 130 engages tissue surrounding filament 120 and causes retainer 130 to fan out from filament 120 and engage the tissue with tissue engagement surface 134 thereby preventing movement of the suture in that direction.

In alternative embodiments, a pledget can be applied to a self-retaining suture. FIG. 1H depicts a pledget 124 located in the transition zone 144 of self-retaining suture system 100. In some embodiments, a pledget 124 can carry a marker/code 128 which helps identify the suture and/or properties thereof. Pledget 124 has one or more apertures 126 through which suture thread 120 can be passed as shown. Alternatively, a pledget can be bonded and/or mechanically fixed to suture thread 120, by, for example, welding, clipping, gluing, fusing. The pledget 126 can be used for locating the transition zone, for providing a stop so that the pledget can be pulled through tissue only until the pledget contacts the tissue, and/or for providing a support to tissue and organs, to name just a few uses. The pledget 126 can take many forms including a wider section that can support tissue.

The ability of self-retaining sutures to anchor and hold tissues in place even in the absence of tension applied to the suture by a knot is a feature that also provides superiority over plain sutures. When closing a wound that is under tension, this advantage manifests itself in several ways: (i) self-retaining sutures have a multiplicity of retainers which can dissipate tension along the entire length of the suture (providing hundreds of "anchor" points this produces a superior cosmetic result and lessens the chance that the suture will "slip" or pull through) as opposed to knotted interrupted sutures which concentrate the tension at discrete points; (ii) complicated wound geometries can be closed (circles, arcs, jagged edges) in a uniform manner with more precision and accuracy than can be achieved with interrupted sutures; (iii) self-retaining sutures eliminate the need for a "third hand" which is often required for maintaining tension across the wound during traditional suturing and knot tying (to prevent "slippage" when tension is momentarily released during tying); (iv) self-retaining sutures are superior in procedures where knot tying is technically difficult, such as in deep wounds or laparoscopic/endoscopic procedures; and (v) self-retaining sutures can be used to approximate and hold the wound prior to definitive closure. As a result, self-retaining sutures provide easier handling in anatomically tight or deep places (such as the pelvis, abdomen and thorax) and make it easier to approximate tissues in laparoscopic/endoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures. The superior qualities of self-retaining suture are particularly beneficial in endoscopic and telesurgical procedures. Self-retaining suture help overcome the limitations of dexterity and sensitivity present in endoscopic and telesurgical instruments.

FIG. 1C shows an endoscopic suture delivery instrument 150 for delivering a self-retaining suture system 100 to a surgical site within a patient. Suture delivery instrument 150 includes, at the proximal end, a handle 152 connected by an elongated tubular member 154 to a spool 156. Handle 152 allows for positioning and operation of the suture delivery instrument 150 from outside of the body of the patient. Handle 152 may include one or more actuators 158 which is, in some embodiments, moved relative to one another and/or handle 152 for operating an effector, such as surgical scissors, a delivery spool, etc., located on the suture delivery instrument.

Elongated tubular member connects handle 152 (proximal end) to spool 156 (distal end). Elongated tubular member 154 is a rigid member which is sized to fit through an access port into the body of the patient. Preferably, the tubular member 154 is about or less than 12 mm, 8 mm and 5 mm. Elongated tubular member 154 must be long enough to reach the desired surgical site through the access port. For laparoscopic instruments, for example, elongated tubular member 154 is between 180 mm and 450 mm in length and is typically 360 mm in length for adults and 280 mm in length for pediatric surgery. Typically the access port will be 12 mm in diameter in less. Preferably the access port will be 10 mm in diameter or less. In some case the access port is, in some embodiments, 8 mm or 5 mm in diameter or less. In general smaller access ports are preferred to reduce trauma to patient tissues however, the parts must be sufficiently large to permit entry of instruments having the functionality to perform the desired surgical manipulations. The diameter of the elongated tubular member 154 and spool 156 will be smaller than the inner diameter of the access port so that the distal portion of suture delivery instrument is, in some embodiments, introduce through the access port.

Figure 1E:
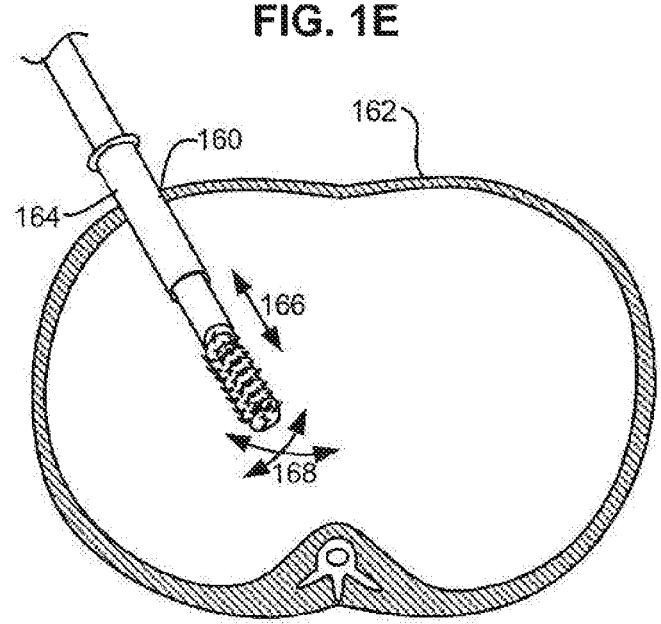
FIG. 1E shows a sectional view of a subject illustrating delivery of a suture using the suture delivery instrument of FIG. 1C.
Figure 1D:
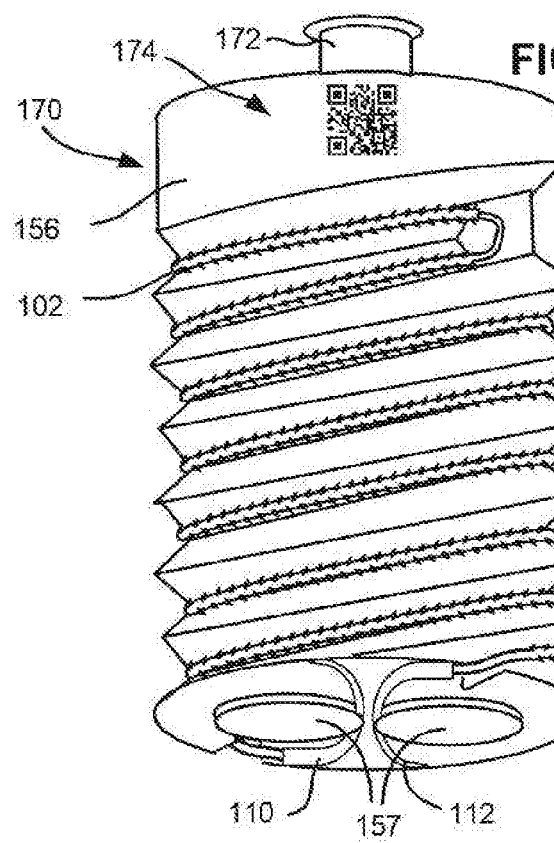
FIG. 1D shows an enlarged view of an embodiment of a suture spool which is, in some embodiments, used with the suture delivery instrument of FIG. 1C according to an embodiment of the present invention.

FIG. 1D shows a cartridge 170 which includes spool 156 and a connector 172. Connector 172 allows cartridge 170 to be releasably attached to the distal end of elongated tubular member 154. In some embodiments, an actuator 158 controls the attaching and releasing of the cartridge 170. A selection of sterile cartridges 170 is, in some embodiments, supplied for a procedure each supporting a different self-retaining suture. Thus, suture delivery instrument 150 can be used by the surgeon or assistant to select and deliver multiple self-retaining suture systems 100 in the course of a procedure. In alternative embodiments spool 156 is, in some embodiments, permanently fixed to the end of suture delivery instrument 150. As shown in FIG. 1D, spool 156 may also include one or more needle docks 157 for supporting the needles 110, 112 of self-retaining suture system 100. Needles 110, 112 are releasable attached to needle docks 157. The needle 110, 112 are removed from needle docks 157 to allow deployment of self-retaining suture thread 102. In some embodiments, needles 110, 112 are replaced in needle docks 157 to allow removal of needles 110, 112 and any surplus self-retaining suture thread 102 after deployment of self-retaining suture thread 102.

As also shown in FIG. 1D, cartridge 170 includes a marker 174. As shown in FIG. 1D, marker 174 is a QR code. A QR code is a machine-readable matrix code or two-dimensional barcode designed to allow quick decoding of its contents. In particular QR codes can be quickly recognized and decoded in camera images. The QR code in some embodiments directly identifies properties of the suture and in other cases identifies the location (URL or other) of data identifying properties of the suture. The properties of the suture are then displayed with the image of the surgical site provided to the surgeon (See FIG. 1G). The information displayed allows the surgeon to verify that the cartridge is loaded with the desired suture. Although a QR code is shown in FIG. 1D, potential markers include, but are not limited to: markers visible in the visible light frequency range; alpha-numeric markers, QR code markers, markers invisible to the naked eye but which can be visualized under the conditions of surgical use; markers recognizable in the non-visible radiation frequency range; markers detectable with ultra-sound; markers which are machine readable; markers which are human readable; markers which is, in some embodiments, read remotely; markers which are active markers (including RFID); and markers which are passive markers (including passive RFID). The properties of the suture which can be associated with the marker include, but are not limited to: length, diameter, material, needles, presence of retainers, absence of retainers, source/brand and/or other fixed properties. In addition to fixed or static properties, a marker can be used to identify dynamic properties. For example, movement of the cartridge and/or suture through forces being placed on the cartridge can cause the marker to move, and such movement can be noted by telesurgical system in order to track the changing location of the cartridge and the suture. Such movement can be translational movement or rotational movement. With the tracking of rotational movement of the spool, for example, the amount of suture removed from the spool can be tracked. Markings placed additionally on the suture can be used to identify the changing location of the suture and also, for example, tension placed on the suture. The markings can also be used with a voice-command telesurgical system. The surgeon speaks the type of suture desired, and the telesurgical system then loads the cartridge onto the end of a tool located on an arm of the telesurgical system for deployment into a patient.

Spool 156 is mounted on the distal end of elongated tubular member 154 and is sized so that it may slide through an access port into the body of the patient. Spool 156 supports self-retaining suture system 100 thus allowing self-retaining suture system 100 to be delivered through an access port to the surgical site within the patient. FIG. 1E shows the distal portion of suture delivery instrument 150 introduced through an access port 160 into a patient 162. Suture delivery instrument 150 is inserted through a cannula 164 at the access port 160. Suture delivery instrument 150 is, in some embodiments, slid in and out of cannula 164 as shown by arrow 166. Suture delivery instrument 150 and cannula 164 may also pivot about the access port 160 as shown by arrows 168. Thus, suture delivery instrument 150 allows spool 156 to be delivered to a surgical site within patient 162.

Figure 1F:
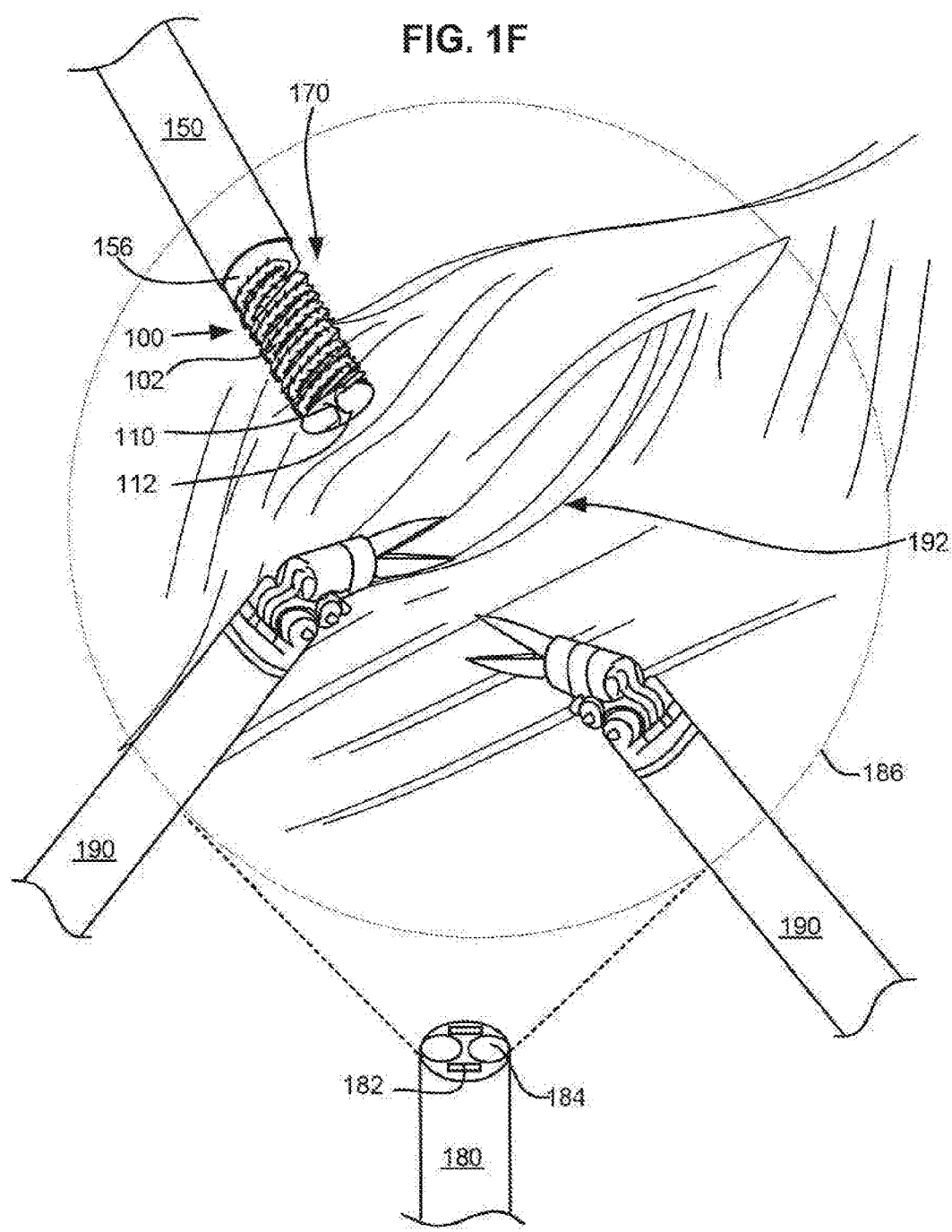
FIG. 1F shows a view of a surgical site illustrating use of the suture delivery instrument of FIG. 1C.

FIG. 1F shows delivery of a self-retaining suture system 100 to a surgical site in a patient. As shown in FIG. 1F, an endoscope 180 illuminates the surgical site with one or more light sources 182. Endoscope 180 also images the surgical site through one or more imaging devices 184. Endoscope 180 thereby illuminates the surgical site. The dashed circle 186 indicates the field of view that is, in some embodiments, transmitted to the surgeon. Note that suture delivery instrument 150 has been inserted so as to position a spool 156 of a cartridge 170 within the field of view. The end effectors (scissors, forceps and the like) of one or more endoscopic surgical instruments 190 also appear in the field of view. The surgeon may operate the endoscopic surgical instruments 190 to grasp the needles 110, 112 supported by spool 156. The surgeon may then operate the endoscopic surgical instruments 190 to deploy self-retaining suture thread 102 into tissue 192. After deployment of self-retaining suture thread 102, the surgeon may operate endoscopic surgical instruments 190 to replace needle 110, 112 in spool 156 and cut off any unused self-retaining suture thread 102. Suture delivery instrument 150 may then be removed from the surgical site thereby removing the needles and any excess self-retaining suture thread 102 from the patient's body.

Figure 1G:
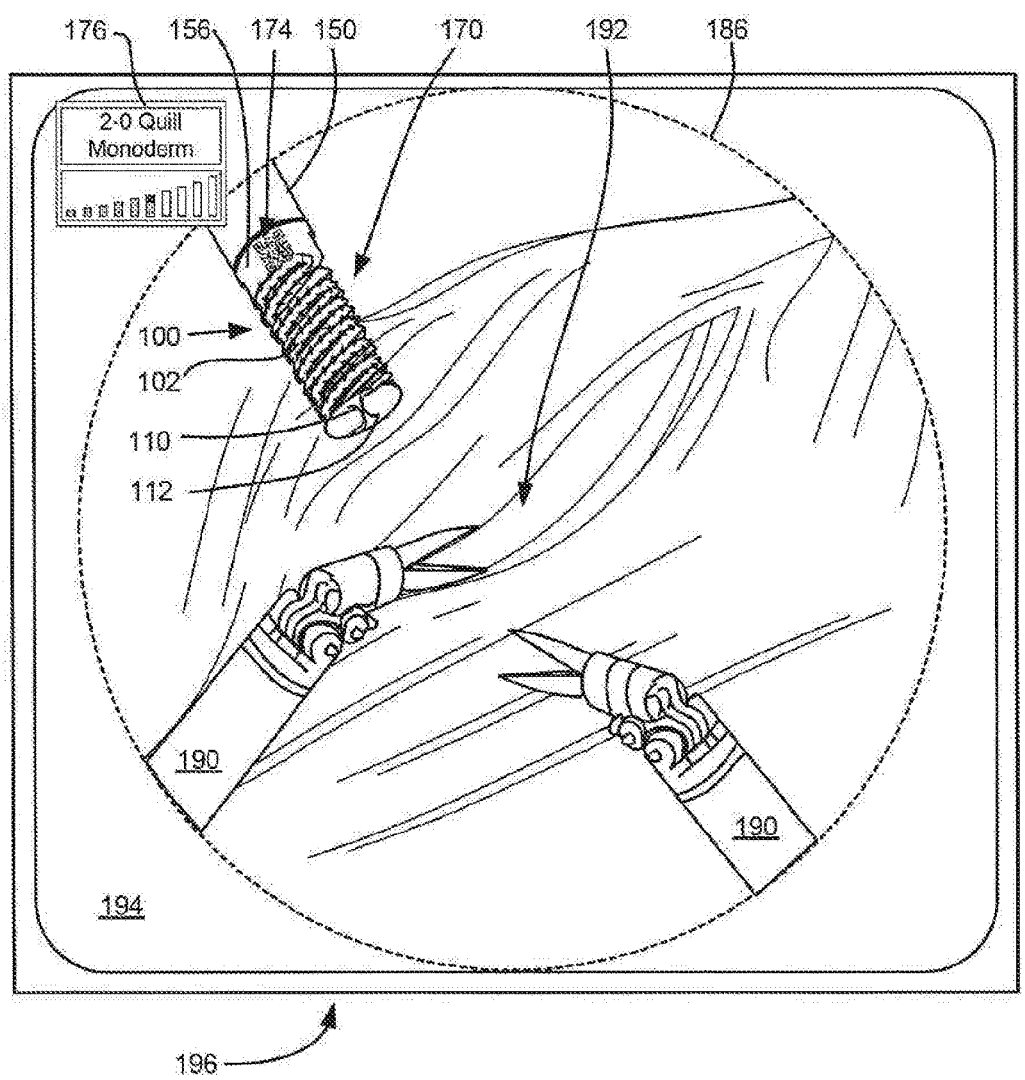
FIG. 1G shows an image of a surgical site provided to a surgeon and illustrating use of the suture delivery instrument of FIG. 1C.

FIG. 1G shows an example of an image 194 on a display 196 of the surgical site of FIG. 1F as displayed to a surgeon. The dashed circle 186 indicates the field of view available from the endoscope (not shown). Note that suture delivery instrument 150 has been inserted so as to position a spool 156 of a cartridge 170 within the field of view 186. Marker 174 of cartridge 170 is visible in the image. A computer system associated with display 196 identifies and translates marker 174. As shown in FIG. 1G, suture property information 176 associated with marker 174 is displayed to the surgeon in the image 194. The information displayed allows the surgeon to verify that the cartridge is loaded with the desired suture. The information displayed can be static or dynamic information. For example, having identified the suture the image display system can also display other suture property information 176 relevant to the suture. For example tension sensed by the endoscopic tools or otherwise can be displayed as a percentage graph of the maximum rated tension of the identified suture.

Robot-Assisted Suture Delivery System

As described above, minimally invasive telesurgical systems have been developed to increase a surgeon's dexterity when working within an internal surgical site, as well as to allow a surgeon to operate on a patient from a remote location. In a telesurgery system, the surgeon is provided with an image of the surgical site at a console. While viewing an image of the surgical site on a suitable display, the surgeon performs the surgical procedures on the patient by manipulating input devices of the console. The input devices control a robot arm which positions and manipulates the surgical instrument. During the surgical procedure, the telesurgical system can provide mechanical actuation and control of a variety of surgical instruments or instruments having end effectors such as, e.g., tissue graspers, cautery, needle drivers, or the like, that perform various functions for the surgeon, e.g., holding or driving a needle, grasping a blood vessel, or dissecting tissue, or the like, in response to manipulation of the master control devices. The Intuitive Surgical, Inc. DA VINCI® Surgical System is one example of a MIS telesurgical system.

In a telesurgical procedure, sutures, including self-retaining suture systems, can in some embodiments be introduced to the surgical site using suture delivery instrument 150 previously described with respect to FIGS. 1C-1G. The suture delivery instrument could be operated manually by the surgeon. However, this requires the surgeon to leave the workstation. Alternatively, the suture delivery instrument 150 can be operated manually by a surgical assistant. However, this requires the assistant to insert the suture delivery instrument manually without the visualization provided by the workstation. According to another embodiment of the present invention, a suture delivery instrument is provided which interfaces with the telesurgery system. The suture delivery instrument is used to deliver the self-retaining suture to the surgical site under the command of the surgeon. Such a suture delivery instrument advantageously leverages the abilities of the telesurgery system to accurately deliver the self-retaining suture to the surgical site under the control of the surgeon at the workstation and using the visualization capabilities of the telesurgery system. Moreover certain portions of the suture delivery operation is, in some embodiments, safely automated to facilitate the repeated delivery and extraction of sutures to the surgical site after initial setup under the control of the surgeon. The surgeon controls the suture delivery instrument with one or more inputs of the console, which can include, for example, switch, keyboards, motion controllers and/or voice input devices.

Figure 2A:
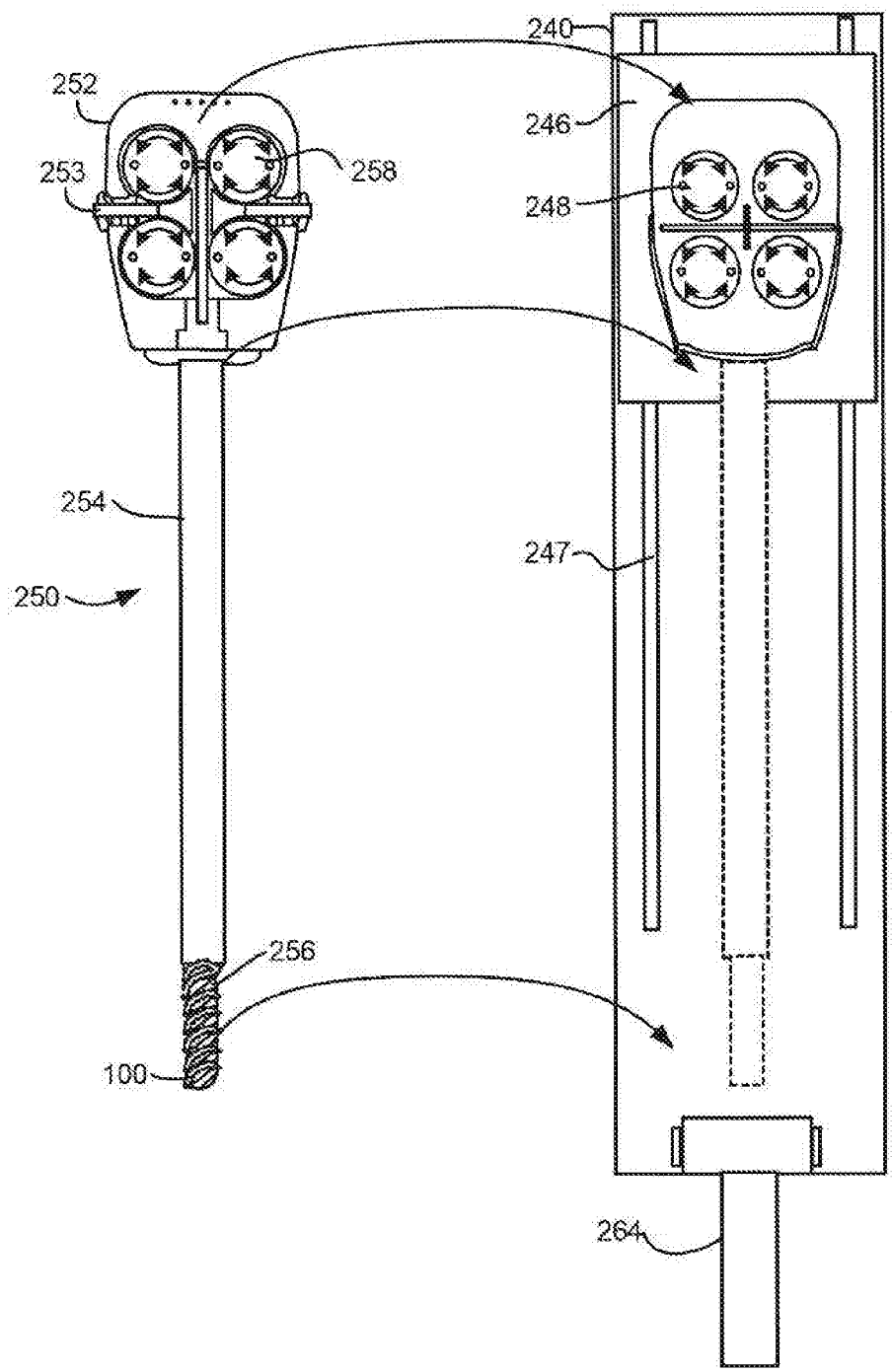
FIG. 2A shows a suture delivery tool suitable for use with a robotically-assisted surgery system in accordance with an embodiment of the present invention; and a surgical manipulator suitable for use with the suture delivery tool.

FIG. 2A shows a suture delivery tool 250 suitable for use with a telesurgery system. Suture delivery tool 250 includes, at the proximal end, a case 252 connected by a tool shaft 254 to an end effector including a spool 256. Case 252 can be mounted to the interface 246 of a manipulator arm 240 to allow for positioning and operation of the suture delivery tool 250 from outside of the body of the patient. Suture delivery tool 250 includes a spool 256 mounted on the distal end of tool shaft 254. Spool 256 supports self-retaining suture system 100 thus allowing self-retaining suture system 100 to be delivered through a cannula/guide 264 to the surgical site within the patient. Spool 256 is sized so that it may slide through cannula/guide 264 into the body of the patient.

Tool shaft 254 connects case 252 (proximal end) to the spool 256 (distal end). Tool shaft 254 is a rigid member which is sized to fit through an access port into the body of the patient. Alternatively, the tool shaft can be flexible. The tool shaft itself can be controlled by the telesurgical system so that the tool shaft can be "snaked" to a desired location. Tool shaft 254 must be long enough to reach the desired surgical site through the access port. The diameter of the tool shaft 254 and spool 256 must be small enough so that the distal portion of surgical tool 250 is, in some embodiments, introduced through the cannula tool guide/access port 264 into the patient. Tool shaft 254 may contain one or more mechanical linkages for transferring motion from the gears 258 in the case to an end effector at the distal end of tool shaft 254.

FIG. 2A also shows the portion of a manipulator arm 240 to which a suture delivery tool 250 is, in some embodiments, mounted. The case 252 of suture delivery tool 250 (or another tool) is, in some embodiments, releasably mounted to the interface 246 on the manipulator arm 240. Case 252 includes one or more clips 253 which engage mating structures on interface 246 to hold case 252 to interface 246. Note that interface 246 can be moved up and down track 247 to slide a tool in and out of cannula/tool guide 264. The movement of interface 246 along track 247 is effected by a transducer/actuator. Track 247 is sufficiently long that when interface 246 is moved to the proximal end of the track (the end furthest from the patient) a suture delivery tool 250 mounted to the interface is completely retracted from the cannula/tool guide 264. Thus, a suture delivery tool 250 is, in some embodiments, mated with or released from interface 246 when interface 246 is at the proximal end of the track. The suture delivery tool 250 may then be inserted through access port 264 using the transducer/actuator to advance interface 246 along track 247 towards the access port 264.

As shown in FIG. 2A, case 252 of suture delivery tool 250 may include one or more gears 258 to control movement/operation of portions of the suture delivery tool 250. Interface 246 includes a plurality of powered gears 248 which mesh with the plurality of gears 258 in case 252 when case 252 is mounted to interface 246. This allows the powered gears 248 of the interface to be utilized to rotate tool shaft 254 and/or spool 256 and/or operate other mechanical operations of the suture delivery tool. For example, suture delivery tool 250 in some embodiments includes at its distal end a grasper for grasping needles for removal from the patient or a cutter for cutting suture during the procedure; the grasper or cutter is, in some embodiments, operated by the powered gears 248 through the mating gears 258 of case 252.

Figure 2B:
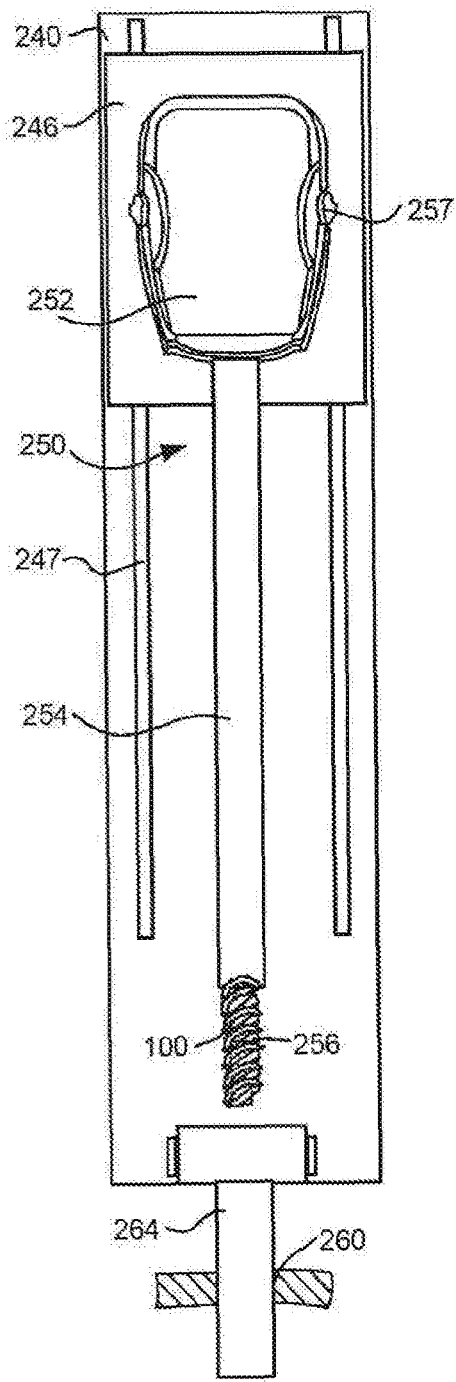
FIGS. 2B and 2C shows introduction of a suture delivery tool by a surgical manipulator in accordance with one embodiment of the present invention.
Figure 2C:
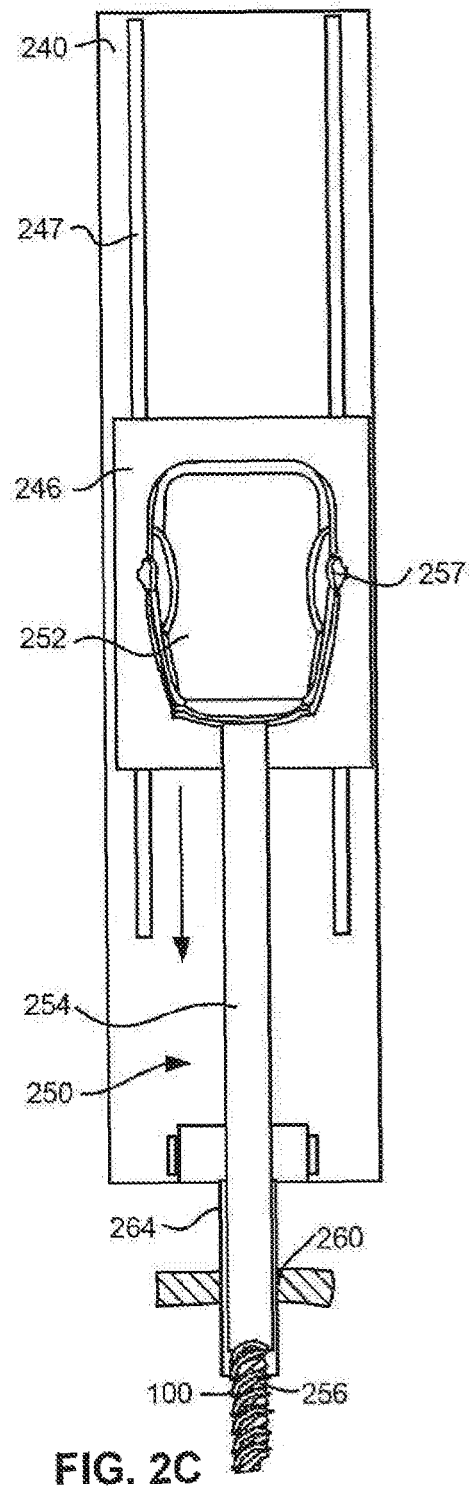

FIGS. 2B and 2C show a suture delivery tool 250 mounted to a manipulator arm 240. The case 252 is held to interface 246 by one or clips 253 (not shown). One or more release levers 257 are accessible when case 252 is mounted to interface 248 to release clips 253 (not shown) when desired. Spool 256 is, in some embodiments, permanently attached to suture delivery tool 250 or may form part of a cartridge which is, in some embodiments, releasably attached to suture delivery tool 250. In some embodiments the spool is permanently or releasably attached at a fixed location of the suture delivery tool 250. Spool 256 is fixed (in this example) at the distal end of suture delivery tool 250. To introduce spool 256 to a surgical site in the subject, the interface 246 is first moved to the proximal end of the track 247 (the end furthest from the patient). The case 248 of the suture delivery tool 250 carrying the spool 256 is then mated with the interface 246 of the manipulator arm 240 as shown in FIG. 2B. The interface 246 is then advanced linearly towards the patient down the track 247. The movement of the interface 246 down the track 247 inserts the spool 256 and the self-retaining suture 100 through the cannula/tool guide 264 into the patient as shown in FIG. 2C. The self-retaining suture 100 may then be positioned at the surgical site within the patient by the manipulator arm 240.

When the spool 256 has been positioned at the surgical site, the self-retaining suture 100 is positioned to be removed from the spool 256 by another instrument. In some embodiments, the needles and surplus suture are reattached to the spool after deployment of the suture. The suture delivery tool delivery tool 250 and spool 256 (and optionally the needles and excess suture) are removed from the body by retracting the interface 246 to the proximal end of the track 247 (the end furthest from the patient) as shown in FIG. 2B. If another suture is required, the suture delivery tool 250 is exchanged for another suture delivery tool, or a cartridge including the spool 256 is removed and replaced with a new cartridge having a new spool 256.

Figure 2D:
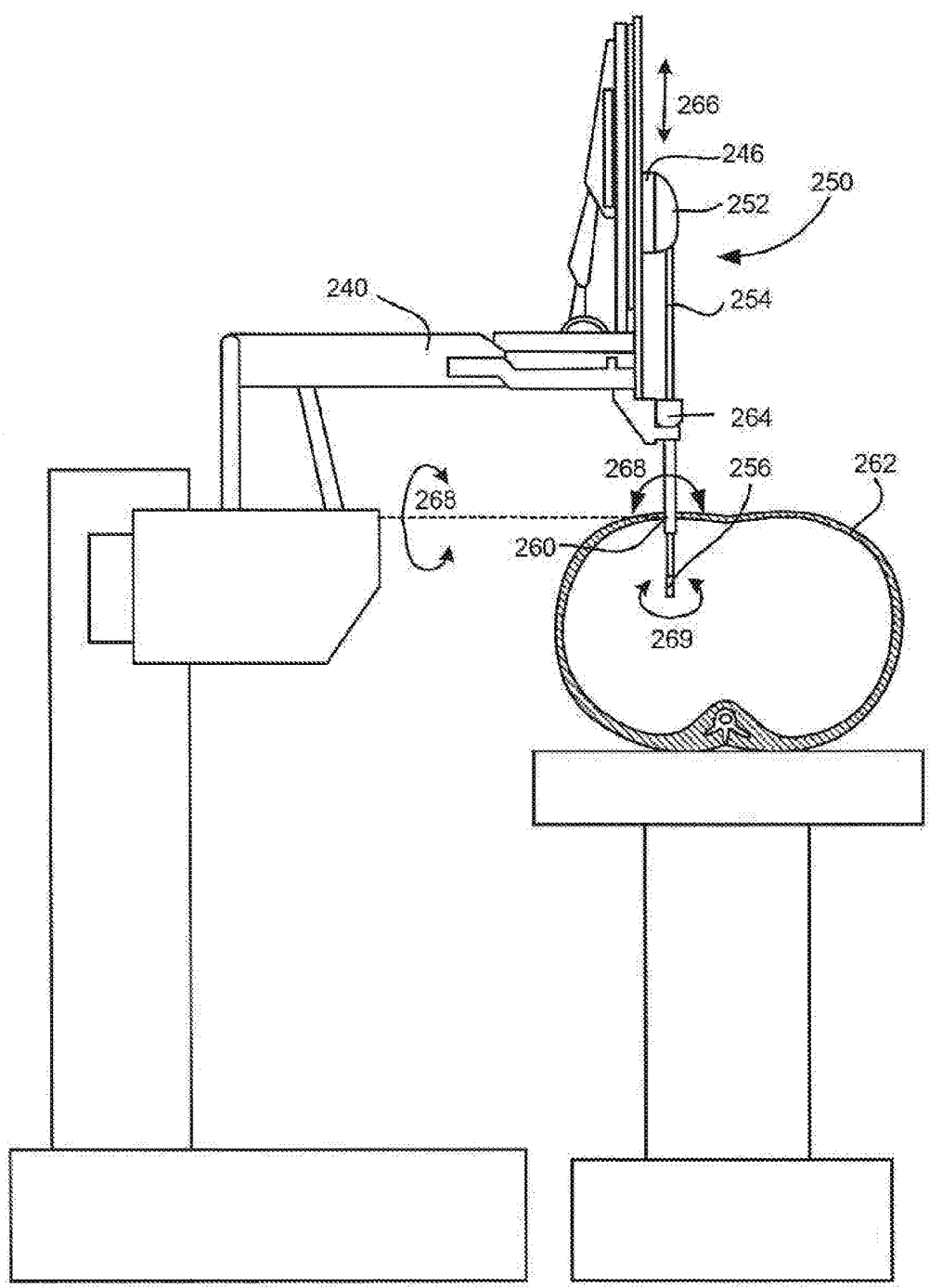
FIG. 2D shows a side view of a suture delivery tool mounted to a surgical manipulator.

FIG. 2D shows a view of manipulator arm 240 with the distal portion of suture delivery tool 250 introduced through an incision 260 into a patient 262. Suture delivery tool 250 is inserted through a cannula 264 at the incision 260. The cannula 264 is coupled to the manipulator arm 240. The suture delivery tool 250 is releasably mated with the interface 246 on the manipulator arm 240. The manipulator arm 240 can position the suture delivery tool 250 and spool 256 in three dimensions and rotate the suture delivery tool 250 about the insertion axis while constraining the motion (preventing lateral displacement) at the incision 260. Suture delivery tool 250 is slid in and out of cannula 264 as shown by arrow 266. Suture delivery tool 250 and cannula 264 is adapted to be pivoted about the incision 260 as shown by arrows 268, 269. The movements of the suture delivery tool in three or more dimensions within patient 262 are thus under the control of manipulator arm 240 allowing the spool 256 and suture 100 to be delivered to a desired position in the operative site and/or within the field of vision of the surgeon.

Figure 2E:
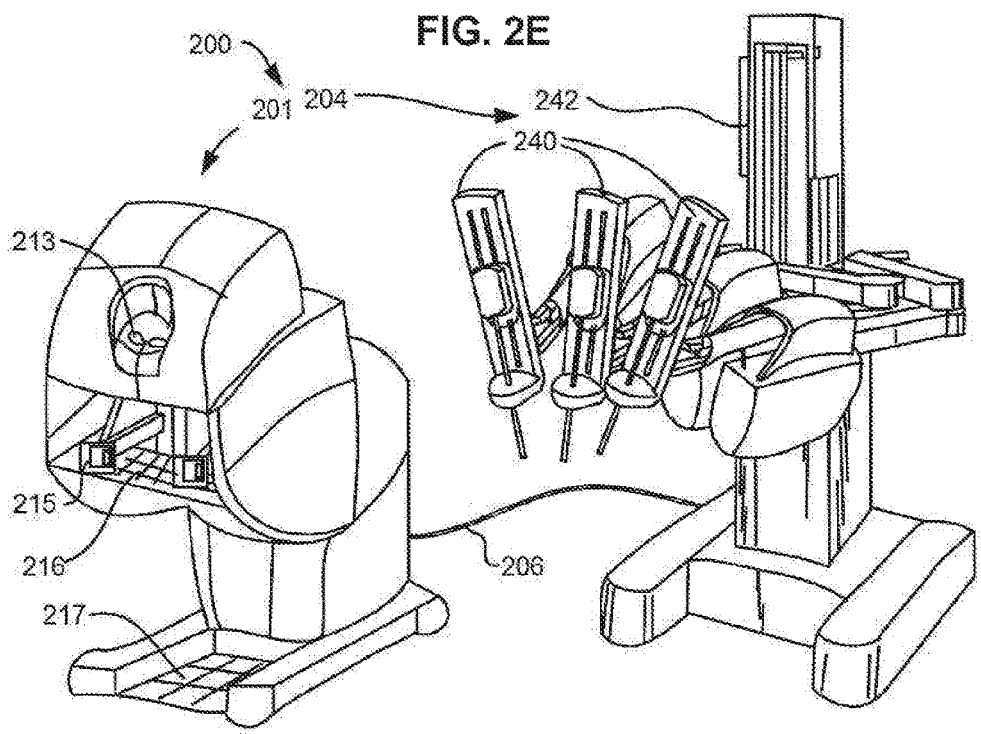
FIGS. 2E and 2F show a surgery system, and a schematic description thereof, for controlling the surgical manipulators and suture delivery tools of FIGS. 2A-2D.
Figure 2F:
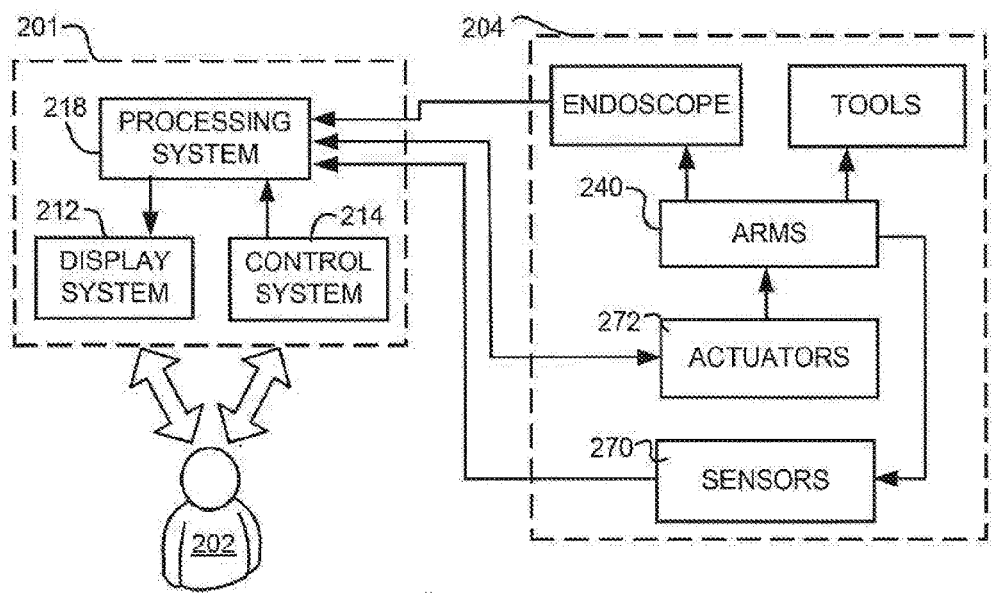

FIGS. 2E and 2F show an example of a telesurgical system 200 which includes a plurality of manipulator arms 240 one of which can be used to position the suture delivery tool 20 within a patient. FIG. 2E shows a perspective view of the telesurgical system whereas FIG. 2F shows a functional block diagram of the telesurgical system 200. As shown in FIGS. 2E, 2F, telesurgical system 200 comprises a patient-side manipulator system 204 and a surgeon's console 201. Patient-side manipulator system 204 includes a plurality of manipulator arms 240 mounted on an adjustable stand 242. The manipulator arms 240 comprise a plurality of mechanical linkages and a plurality of transducers/actuators. The transducers/actuators are, in some embodiments, electrical motors, for example, stepper motors and/or servo motors. In alternative embodiments, the actuators are pneumatic, hydraulic, magnetic or other transducers capable of effecting movement of the linkages in response to control signals. The position of the linkages is monitored using a plurality of sensors 270; e.g. linear or rotary optical encoders. The linkages are adapted to be moved independently by a plurality of actuators 272; e.g. stepper motors and shape-memory actuators. In some cases, the actuators 272 may also be sensors 270; for example, stepper motors function as actuators, position encoders and force sensors.

The endoscope, suture delivery instrument and one or more surgical tools are coupled to the manipulator arms 240. The number of patient-side manipulators and instruments used will vary depending on the procedure. A patient-side manipulator system 240 in some embodiments includes two mechanical manipulator arms 240 for operating surgical tools and one manipulator arm 240 for positioning the endoscope. A suture delivery tool is in this embodiment positioned and operated by one of the two manipulator arms 240 for operating surgical tools. A suture is in some cases inserted with the suture delivery tool 250 and then the suture delivery tool exchanged for another surgical tool such as a needle driver or grasper. In some systems, a fourth arm is provided. In such systems the suture delivery tool is positioned and operated by the fourth manipulator arm. The surgeon can switch between control of the surgical instruments and control of the suture delivery tool without the need for exchange of the suture delivery tool with a surgical instrument.

Surgeon's console 201 comprises a display system 212, a control system 214 and a processing system 218. The display system 212 includes a 2D or 3D video display 213 and one or more of an audio output system, force-feedback system, touchscreen display and other display elements e.g. lights, buzzers etc. The display system 212 provides the surgeon 202 with an image of the surgical site and may also provide other information in visual, audible and/or haptic formats. The control system 214 may include one or more of a variety of input devices; for example hand-operated controllers 215, joysticks, gloves, keyboards 216, buttons, case-pedals 217, touchscreen displays, mice and the like. A microphone may also be provided so that the surgeon can provide voice commands to the control system. Particular components are elements of both display system 212 and control system 214; for example, force-feedback hand controllers and touchscreen displays which both display information and receive input.

The surgeon 202 performs a minimally-invasive surgery procedure by manipulating control devices of the control system 214. The output of the control system 214 is received by a processing system 218. One function of processing system 218 is to translate the output of the control system 214 into control signals for the operation of the patient-side manipulator system 204. Surgeon's console 201 is connected by cable 206 to patient-side manipulators 240 and 242. The operation of the control devices by the surgeon 204 operates the patient-side manipulator system 204 and manipulator arms 240 to position and operate surgical tools and an endoscope coupled to the manipulator arms 240. The movement of the surgical tools is imaged by the endoscope and the image of the surgical tools is transmitted to the processing system 218. The processing system transforms the image of the surgical tools and transmits it (and other information) to display system 212 so that it can be observed by the surgeon 202.

FIGS. 3A and 3B show an alternative suture delivery tool 350 mounted to a manipulator arm 240. Suture delivery tool 350 has a load slot 310 for receiving a cartridge 320 including a spool 356. Cartridge 320 is sized and configured to fit through load slot 310 into the tool shaft 354 as shown in FIG. 3A. Suture delivery tool 350 has a transport mechanism 312 for moving cartridge 320 from the loading slot 352 to the distal end of suture delivery tool 350 where it is accessible through delivery slot 314 for removal of the suture 100. In some embodiments, the driven gears 248 of a manipulator arm 240 operate the transport mechanism through mating gears (not shown) in the case 352. The transport mechanism 312 is for example a cable drive screw drive or similar drive for moving a cartridge linearly through the tool shaft 354.

To introduce spool 356 to a surgical site in a patient, the distal end of the suture delivery tool 350 is first positioned at the surgical site under surgeon control. Cartridge 320 is then loaded into the loading slot 310 of the suture delivery tool 350. The transport mechanism 312 is then operated to move the cartridge 320 from the loading slot 310 to the delivery slot 314 at the distal end of suture delivery tool 350 as shown by arrow 317. When cartridge 320 reaches the distal end of suture delivery tool 350, cartridge 320 is exposed sufficiently at delivery slot 314 that the suture and needles are exposed to be accessed and removed from the cartridge 320 as shown in FIG. 3B. The self-retaining suture 100 is then removed from the cartridge 320 by another surgical instrument at the surgical site. In some embodiments, the spool 356 can be rotated at the delivery slot 314 in order to remove the suture from the spool. In some embodiments, the needles and surplus suture are re-attached to cartridge 320 after deployment of the self-retaining suture 100. The cartridge 320 is then removed from the body by operating the transport mechanism 356 in the opposite direction to retract the cartridge 320 from the delivery slot 314 to the loading slot 310 where the cartridge 320 is positioned to be removed and replaced with a new cartridge 320.

Advantageously, one or more cartridges 320 are delivered through suture delivery tool 350 automatically. The automatic delivery of cartridges is rendered safe by the fact that the cartridge 320 stays within the confines of the suture delivery tool 350. Additionally, the suture delivery tool itself does not change position during automatic delivery of the cartridge (only the cartridge is moved). Once the suture delivery tool has been positioned under surgeon guidance, there is little or no possibility of the insertion or retraction of a new cartridge 320 causing damage to tissue at the surgical site. Thus the presentation and removal of suture cartridges 320 is performed automatically or by the surgeon's assistant without the need to check the position for delivery of subsequent cartridge deliveries.

FIG. 3C shows one embodiment of a suture delivery tool 350 which is adapted to move a cartridge 320 from a proximal end of the shaft 354 to the distal end of the shaft 354. FIG. 3D shows a section through the tool shaft 354. FIGS. 3E and 3F show views of one embodiment of a cartridge for use with suture delivery tool 350 of FIG. 3C. FIG. 3C shows interior components of case 352 and tool shaft 354. As shown in FIG. 3C, transport mechanism comprises a threaded rod 316 which runs the length of tool shaft 354. The threaded rod 316 is supported at each end by a bushing which allows rotation of the threaded rod. A capstan 360 within case 352 is directly connected to a gear of case 352 which is adapted to be mated with a driven gear of the interface of the manipulator arm. A transmission mechanism transmits rotation of capstan 360 to rotation of threaded rod 316. The transmission mechanism is, in some embodiments, a geared mechanism or may comprise a pulley-driven system as shown in FIG. 3C. As shown in FIG. 3C a loop of cable 364 is wrapped around capstan 360 and idler pulley 364 between capstan 360 and idler pulley 364, cable 364 is also wrapped around a pulley 366 mounted to threaded rod 316. Thus, when capstan 360 is turned by a driven gear of the manipulator arm the threaded rod is rotated. When a cartridge 320 is inserted into the loading slot 310 a groove 322 in the cartridge 320 engages the threaded rod 316.

When cartridge 320 is engaged with threaded rod 316, rotation of threaded rod 316 results in movement of the cartridge up or down tool shaft 354 depending on the direction of rotation of the threaded rod 316. Threaded rod 316 can be rotated in one direction to move cartridge 320 from the load slot 310 to the delivery slot 316. Threaded rod 316 can be rotated in the opposite direction to move cartridge 320 from the delivery slot 316 back to the load slot 310 where it can be removed/replaced. Note that in some embodiments, what is shown as a cartridge in FIG. 3C is a shuttle which is an integral part of the suture delivery tool 350. In such embodiments, rather than removing and replacing a cartridge, sutures are loaded and unloaded from the shuttle to be transported to or from the distal end of the suture delivery tool 350.

FIG. 3D shows a sectional view through shaft 354 along the line D-D of FIG. 3C. The position of a cartridge 320 within the shaft is shown by the dashed line. Note that the interior of groove 322 is pushed against and engaged with threaded rod 316. Note also that shaft 354 has an internal ridge 318 which also engages groove 322 to prevent rotation of cartridge 320.

FIGS. 3E and 3F show one embodiment of a cartridge 320 suitable for use with the suture delivery tool 350 of FIGS. 3C and 3D. As shown in FIG. 3E cartridge 320 comprises a cylinder several centimeters long and having a diameter slightly less than the interior diameter of shaft 354. Cartridge 320 has a groove 322 in the back surface. Groove 322 is sized to fit over the threaded rod 316 and ridge 318 of suture delivery tool 350. Groove 322 has surface features 324 for engaging threaded rod 316. Surface features 325 include, for example, threads, ridges or similar contact points which can engage threaded rod 316 to cause linear motion of cartridge 320. Cartridge 320 has an opening 321 on the front surface through which a self-retaining suture 100 is loaded into the hollow chamber 326. Hollow chamber contains needle docks 328 for releasably securing needles 110, 112 of self-retaining suture 100. Suture thread 102 is positioned linearly within hollow chamber 326 passing around pin 329 to hold self-retaining suture 100 in position during transfer. Where longer suture is required self-retaining suture 100 is coiled up with cartridge 320. Cartridge 320 may additionally comprise more needle docks and nubs so that cartridge 320 can hold two or more self-retaining sutures 100.

C. Suture Cartridges for Suture Delivery Systems

FIGS. 4A through 4G show various suture cartridges suitable for use with MIS suture delivery tools in accordance with embodiments of the present invention. In general, the cartridge should have a diameter less than the diameter of the access port i.e. typically the cartridge should be 10 mm in diameter or less. The cartridge length will be determined by the amount of suture to be contained. As a practical matter, the cartridges will preferably be a fraction of the length of the suture delivery tool. Thus, the cartridges will preferably be 120 mm or less in length and more preferably 80 mm or less in length. In some circumstances, the cartridges are 10 mm or less in length. The cartridge should also have a coupling, aperture groove or the like for attaching the cartridge to the suture delivery tool or engaging the drive mechanism of the suture delivery tool. Each of the cartridges and spools discussed herein is adaptable for use with each of the suture delivery tools discussed herein by addition of the appropriate mating features for engaging the suture delivery tool.

FIG. 4A shows a cartridge 410 comprising a spool 412 having a helical groove 414. As shown in FIG. 4A, self-retaining suture 100 is wrapped around spool 412 within helical groove 414. In preferred embodiments, the cartridge includes a mechanism for preventing tangling of the suture or self-retaining suture. For example, with respect to cartridge 410, the retainers of section 142 facing in a given direction are spaced apart from the retainers of section 146 facing in an opposing direction (and which is separated from section 142 by transitional segment 144). The self-retaining suture 100 is, in some embodiments, wrapped sufficiently tightly around spool 412 that the retainer pluralities do not overlap with one another; for example, needles 110 and 112 at either end of self-retaining suture 100 are, in some embodiments, removably engaged in needle parks 416 and 417, respectively, in order to achieve such tension.

Note helical groove 414 is sufficiently deep that the suture 100 does not protrude above the ridges between turns of groove 414. It is to be understood that in this particular embodiment that friction engagement structures can be used to retain the suture 100 to the spool 412 in place in grooves. Note that suture 100 must be unwound from spool 412 thus requiring that spool 412 is mounted in a fashion that allows it to rotate or mounted without obstruction to unwinding the suture 100 from the spool 412. As shown in FIG. 4A, cartridge 410 has a central aperture 418 for mounting cartridge on a pin on the end of a suture delivery tool (for example suture delivery tool 150 of FIG. 1C or suture delivery tool 250 of FIG. 2A. The aperture is provided with a latching mechanism such that the pin is releasably retained within aperture 418 while still allowing rotation of cartridge 410 during removal of self-retaining suture 100.

FIG. 4B shows a partial cutaway view of a variation of cartridge 410 of FIG. 4A. In the embodiment of FIG. 4B the spool 412 is provided with a cover 430 which fits over the spool 412, holding suture 100 within groove 414. Suture 100 can be removed by sliding cover 430 off spool 412 (incrementally or in one go). Alternatively, cover 430 is made of a material that can be split by the suture as the suture 100 is unwound. Cover 430 may, for example, be perforated along the groove 414 so that suture 100 is adapted to be pulled through the cover 430 as it is unwound from the spool 412. Such a cover may also be used with other cartridges described herein. A cover is useful to protect the suture during delivery to the surgical site and to retain the suture within the cartridge during delivery. In some embodiments the cover is removed by the surgeon using another surgical instrument. In other embodiments, the cover is removed by actuation of the suture delivery tool to which the cartridge is mated.

As shown in FIG. 4C, self-retaining suture 100 is wrapped around spool 422 within double helical grooves 424. The retainers of section 142 facing in a given direction are spaced apart from the retainers of section 146 facing in an opposing direction (and which is separated from section 142 by transitional segment 144). The self-retaining suture 100 is, in some embodiments, wrapped sufficiently tightly around spool 422 that the retainer pluralities do not overlap with one another. For example, needles 110 and 112 at either end of self-retaining suture 100 are, in some embodiments, removably engaged in needle parks 426 and 427 and transitional segment 144 can be wrapped around pin 423, respectively, in order to achieve such tension. Note helical groove 424 is sufficiently deep that the suture 100 does not protrude above the ridges between turns of grooves 424. It is to be understood that in this particular embodiment that friction engagement structures can be used to retain the suture 100 to the spool 422 in place in grooves. Note that suture 100 must be unwound from spool 422 thus requiring that spool 422 is mounted in a fashion that allows it to rotate or mounted without obstruction to unwinding the suture 100 from the spool 422. As shown in FIG. 4A, cartridge 420 has a central protrusion 428 for mounting cartridge on the end of a suture delivery tool, for example, suture delivery tool 150 of FIG. 1C or suture delivery tool 250 of FIG. 2A. The protrusion is provided with a latching mechanism 429 such that the protrusion is releasably retained within a suture delivery tool while still allowing rotation of cartridge 420 during removal of self-retaining suture 100.

Groove 414 or grooves 424 are, in some embodiments, provided with retaining features to releasably retain self-retaining suture 100 to manage self-retaining suture 100 while it is being unwound form a spool. For example, as shown in FIG. 4D, the groove is shaped so that the adjacent walls of the grooves are approximately parallel and slightly closer together than the diameter of the suture 100. The walls thus serve to keep suture 100 in the groove even when the tension in suture 100 is released. The walls are flexible enough that they can be pushed apart with a slight force to admit and release suture 100 as it is being wound on or off of the spool. This configuration of helical groove forms what is essentially a continuous helical clip which lightly holds suture 100 to the surface of the spool. Other configurations of groove and clips are used in alternative embodiments to hold suture 100 in place. For example, releasable clips are positioned intermittently along the helical groove. Alternatively, a releasable adhesive or gel is provided continuously or intermittently along the helical grove to retain suture 100 in the absence of tension. The spools of the various embodiments herein hold the sutures so as not to compress or reposition the retainers. Generally, the retainers on the suture are proud. That is, the retainers stand out or away from the body of the suture. In a container or cartridge such as a spool, it may be desirable that the retainers to remain away from the body of the suture and not be compressed against the body of the suture. Further, it is to be understood that some materials such as polymers, that the suture body is made up can have a memory. That is to say, the suture can develop a set shape after being help in a certain shape for awhile, such as being held in a container. With a spool, the suture can be set or have a memory of a suture with many small loops. This can be advantageous in a situation where tight radius suturing is desirable. With the suture set with tight loops, the suture can be managed as the suture is in a coil and the tight loops of the suture help facilitate sewing tissue with tight radius stitches. Further, with these cartridges, drug can be coated on the internal surfaces of the cartridges such that as the suture is removed from the cartridges, drugs coated on the surfaces of the helical grooves, for example, can rub off onto the suture for delivery to the tissue.

Cartridges 410 and 420 are preferably 10 mm or less in diameter so that they may fit through a cannula/guide into a patient. The length of cartridges 410, 420 may vary depending upon the length of self-retaining suture 100 and the number of turns of the groove required to hold self-retaining suture 100. For example, if spools 412, 422 are 10 mm in diameter, approximately 30 mm of suture will be taken up by one wrap around the spool. Thus, a suture of 70 mm total length will require less than three turns of groove around the spool. A suture of 140 mm total length will require less than five turns of groove around the spool. These three to five turns of groove may readily be provided in a cartridge 10 mm in a spool 10 mm or less in length. This allows three to five cartridges of 10 mm or less in length to be mounted to the end of a suture delivery tool to allow the introduction of multiple self-retaining sutures to a surgical site at the same time. As shown in FIG. 4E, a suture delivery tool 450 includes a spindle 452. A plurality of cartridges 454 each holding a self-retaining suture 100 including needles is received over spindle 452. Each cartridge 454 has a central aperture 455 which fits over spindle 452. Spindle 452 has at its distal end a catch 456 for releasably retaining the plurality of cartridges onto the spindle 452 during use. Additional catches 456 is, in some embodiments, provided along the length of spindle 452 so that less than the maximum number of cartridges is, in some embodiments, securely held on the spindle 452.

Figure 4F:
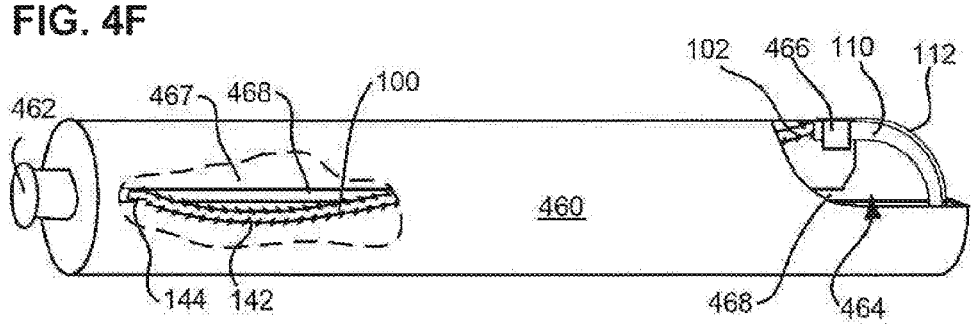
Figure 4G:
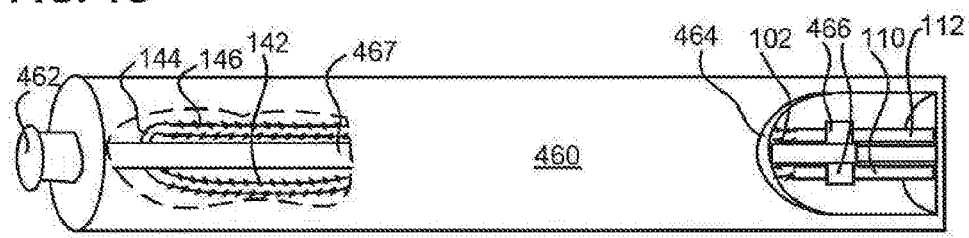

FIGS. 4F and 4G show two partial cutaway views of a suture cartridge 460 suitable for use with MIS suture delivery tools in accordance with embodiments of the present invention. In cartridge 460, self-retaining suture 100 is arranged in a linear configuration. The linear configuration is suitable for shorter sutures which are often used in MIS surgery. For example, in one embodiment, self-retaining suture 100 is, in some embodiments, approximately 70 mm in total length with each of sections 142 and 146 being approximately 35 mm in length. Cartridge 460 would be approximately 40 mm in length to accommodate the 70 mm suture in the configuration of FIG. 4F. In another embodiment, self-retaining suture 100 is, in some embodiments, approximately 140 mm in total length with each or sections 142 and 146 being approximately 70 mm in length. Cartridge 460 would be approximately 80 mm in length to accommodate the 140 mm suture in the configuration of FIG. 4F.

As shown in FIGS. 4F and 4G, cartridge 460 is approximately cylindrical and has a projection 462 on its proximal end for releasably engaging a suture delivery tool. Cartridge 460 has an opening 464 at its distal end for allowing access to the interior of cartridge 460. Adjacent opening 464 there are a plurality of needle docks 466 for releasably holding a plurality of needles. As shown in FIGS. 4F and 4G, a self-retaining suture 100 is contained with cartridge 460 with needles 110 and 112 releasably secured adjacent opening 464 by needle docks 466. A longitudinal divider 467 separates sections 142 and 146 of self-retaining suture 100. Section 144 of self-retaining suture 100 passes through a slot 468 in divider 467. When deployed self-retaining suture 100 can be pulled along/through slot 468 towards opening 464. Slot 468 is open with opening 464 allowing self-retaining suture 100 to be released from the cartridge 460.

Figure 4H:
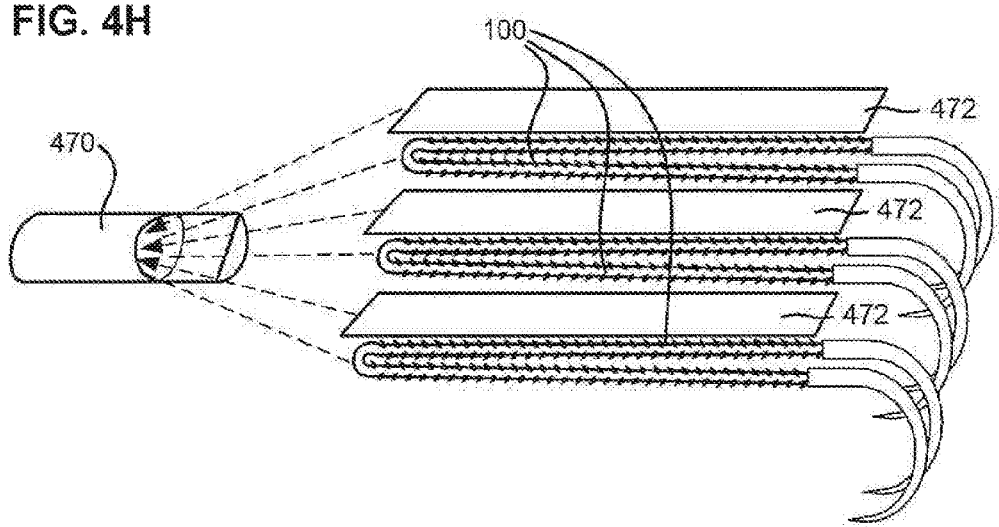

The cartridge 460 may include several different sutures in similar configurations and spaced from one another by dividers or the like. As shown in FIG. 4H, multiple loops of suture 100 are separated from one anther by dividers 472 so that each suture is, in some embodiments, removed individually from a cartridge. The stacked sutures may then be loaded into a suture cartridge 470. Cartridge 470 has sufficient needle docks for each of the needles of the sutures. In use, the surgeon may remove one suture and its associated needles at a time without disturbing the other sutures 100.

Suture Cartridge Magazine for Suture Delivery Systems

In some situations, it is, in some embodiments, desirable to automate the delivery, loading and exchange or suture delivery cartridges to a suture delivery tool in a telesurgery system. In one example, where telesurgery is to be performed at a remote location, there is, in some embodiments, no patient-side assistant to load cartridges onto a suture delivery system. In another example, it is, in some embodiments, more expedient or reliable to let the surgeon select a suture of choice using the surgeon's console as an interface rather than relying upon communication between the surgeon and a patient-side assistant. A suture cartridge magazine holds a plurality of suture cartridges. A selector mechanism allows a surgeon to select a cartridge to be loaded into a suture delivery tool from the cartridges available in the magazine. A cartridge load/unload mechanism loads the cartridge onto/into the suture delivery tool and unloads the cartridge after deployment of the suture. This allows the surgeon to choose a suture and deploy it to the surgical site using the surgeon's console controls without the use of an assistant.

FIGS. 5A-5C show a suture cartridge magazine 500 which is adapted to select, load and unload cartridges 520 into a suture delivery tool 550 mounted to a manipulator arm 540. The case 552 of suture cartridge magazine 500 is releasably mounted to the interface 546 on the manipulator arm 540. Magazine 500 is, in this embodiment, mounted to interface 546 adjacent a load slot 522 in suture delivery tool 550. Thus, in this embodiment, magazine 500 is in a fixed position relative to suture delivery tool 550. In other embodiments, such as where a cartridge is loaded at the distal end of a suture delivery tool, magazine 500 is, in some embodiments, mounted in an affixed position relative to manipulator arm 540. In such case, the suture delivery tool retracts to place the distal end of the tool in position for loading and is then advanced into the patient.

As shown in FIGS. 5A-5C, a support 502 is mounted to interface 546. Support 502 carries a selector mechanism 504 and a load/unload mechanism 506. Magazine 500 is hooped shaped an has a plurality of spring loaded bays 508 each of which is adapted to releasably secure a cartridge. The number of bays can be selected based on the needs of the system. The bays 508 are open towards the interior and exterior of the magazine. However, a cover 510 substantially covers the magazine 500 such that only one bay 508 is exposed at an opening 512 at any time. The bays can rotate with respect to cover 510 so that any one of the bays 508 is, in some embodiments, adjacent the opening 512. Magazine 500 mounts to support 502 such that opening 512 in cover 510 is adjacent to suture delivery device 550.

Selector mechanism 504 engages magazine 500 such that it rotates bays 508 past opening 512 and suture delivery tool 550 as shown by arrow 514 of FIGS. 5A and 5B. Selector mechanism 504 may rotate bays 508 passed opening 512 for sequential loading of cartridges 520. Alternatively, as cartridges 520 is, in some embodiments, loaded with different sutures, it is, in some embodiments, desirable to allow selectable loading and unloading of any one of the cartridges. Data regarding the sutures is, in some embodiments, entered into the system manually upon loading the magazine, or more preferably, each cartridge comprises a machine readable device, such as a barcode or RFID tag, which identifies the suture loaded on the cartridge. The system can thus automatically determine the sutures available in a magazine and the position of the respective cartridges in the magazine by reading each machine readable device in sequence when the magazine is loaded. The surgeon's console should display data regarding the sutures available in cartridges available in the magazine to the surgeon and allow the surgeon to select a suture for use in the procedure. When the surgeon selects a suture, thus selector system 504 indexes magazine 500 until the desired cartridge 520 is positioned adjacent opening 512 and suture delivery tool 550. The selector system 504 is preferably operated by one or more transducers/actuators controlled by the surgeon from the surgeon's console. In some embodiments selector system 504 may coupled to a driven gear 248 (See FIG. 2A) of interface 546.

When the desired cartridge 520 is positioned adjacent opening 512 and suture delivery tool 550, load/unload mechanism 506 is activated to push the cartridge 520 from the spring-loaded bay 508 through opening 512 and into the load slot 522 of the suture delivery tool 550 (see arrow 516 in FIG. 5C). The transport mechanism of the suture delivery tool can then be activated to transport cartridge 520 to the distal end of suture delivery tool 550 for deployment of the suture. After deployment, cartridge 520 is transported back to the load slot of suture delivery tool 550. Load/unload mechanism 506 is then activated to pull cartridge 520 from the load slot into the spring-loaded bay 508. A new suture may then be selected by the surgeon and the cartridge indexed and loaded automatically in response to the suture selected by the surgeon. The load/unload mechanism 506 is operated by one or more transducers/actuators controlled by the surgeon from the surgeon's console. In some embodiments load/unload mechanism 506 may coupled to a driven gear 248 (See FIG. 2A) of interface 546.

Note that all of the suture delivery systems described herein are, in some embodiments, utilized for the delivery of plain sutures. Moreover, the suture delivery systems are, in various embodiments, used for the delivery of self-retaining sutures in a wide variety of configurations including unidirectional self-retaining sutures, unidirectional self-retaining sutures having an anchor at one end and a needle at the other end; and/or bidirectional self-retaining sutures as discussed herein.

Figure 6A:
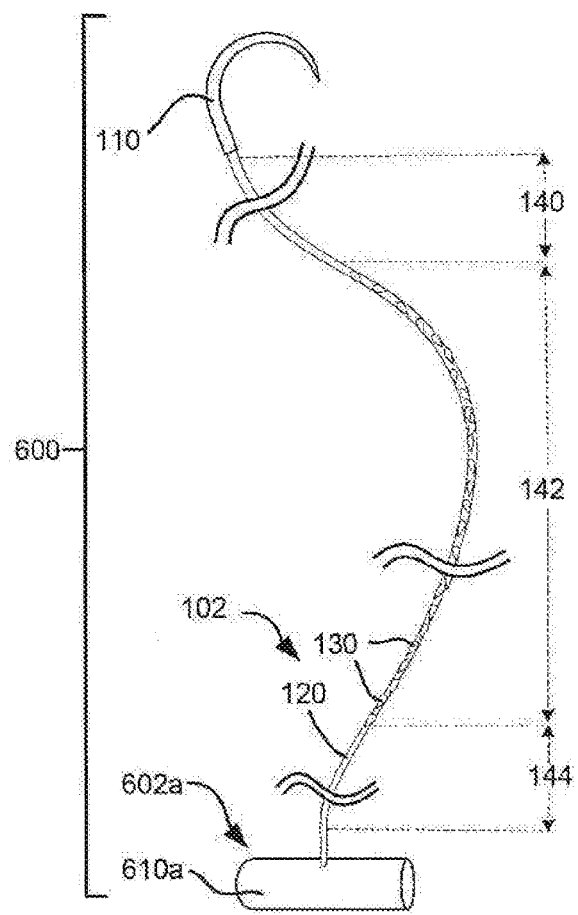
FIGS. 6A-6D show alternative self-retaining suture systems which have an anchor at one end.

FIG. 6A illustrates an alternative embodiment of a self-retaining suture system 600. Self-retaining suture system 600 includes needle 110 and sections 140, 142 and 144 of self-retaining suture system 100 of FIG. 1A. However, self-retaining suture system 600 is a single-armed system. As shown in FIG. 6A, filament 120 terminates following section 144 in a tissue anchor 602a. Tissue anchor 602a is a device for engaging tissue and preventing filament 120 from moving through tissue in the direction of needle 110. Tissue anchor 602a is in some embodiments formed in one piece with filament 120 or formed separately and subsequently attached to filament 120. As shown in FIG. 6A, tissue anchor 602a has a bar-shaped body 610a which extends approximately perpendicular to the axis of filament 120. Bar-shaped body 610a is sufficiently long and stiff to preclude movement of the distal end of filament 120 in the direction of needle 110 after tissue anchor 602a has engaged a tissue.

Figure 6B:
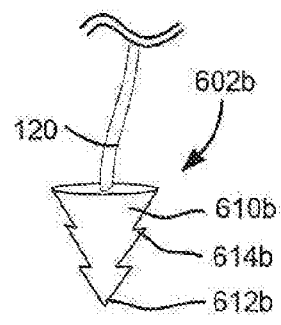

FIG. 6B shows an alternative anchor 602b which could be used in place of tissue anchor 602a of FIG. 6A. As shown in FIG. 6B, tissue anchor 602b comprises a conical body 610b. Conical body 610b has a pointed end 612b and tissue engaging features 614b which consist of ribs and/or barbs. Tissue anchor 602b is configured to be pushed into tissue in order to anchor filament 120 to that tissue and preclude movement of the distal end of filament 120 in the direction of needle 110.

Figure 6C:
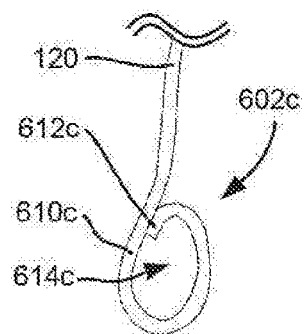

FIG. 6C shows an alternative tissue anchor 602c which could be used in place of tissue anchor 602a of FIG. 6A. As shown in FIG. 6C, tissue anchor 602c comprises a loop 610c. Loop 610c is, in this embodiment, formed by folding back the end 612c of filament 120 and securing end 612c to filament 120 by welding, fusing and/or adhesive. Loop 610c is thus formed from the material of filament 120. Loop 610c has an aperture 614c through which needle 110 can pass in order to create a noose/cinch which can be used to engage tissue and preclude movement of the distal end of filament 120 in the direction of needle 110.

Figure 6D:
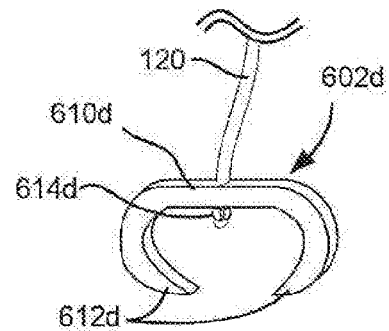

FIG. 6D shows an alternative tissue anchor 602d which could be used in place of tissue anchor 602a of FIG. 6A. As shown in FIG. 6D, tissue anchor 602d comprises a staple-shaped body 610d. Filament 120 passes through an aperture in anchor 602d and is secured by a crimp 614d. Staple-shaped body 610d has two pointed ends 612d which can be pushed into tissue and deformed towards each other to engage the tissue and preclude movement of the distal end of filament 120 in the direction of needle 110.

Figure 6E:
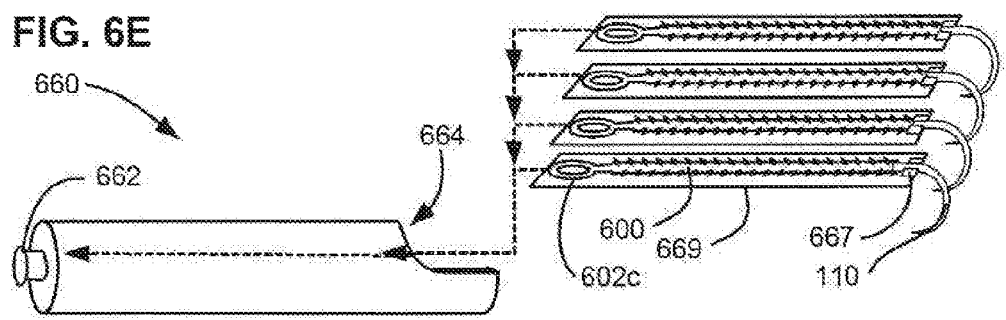
FIGS. 6E-6F show views of a cartridge for holding one more of the alternative self-retaining suture systems of FIGS. 6A-6D.
Figure 6F:
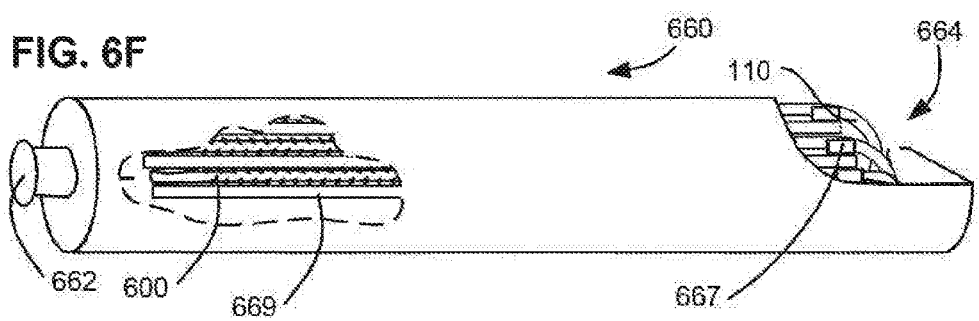

FIGS. 6E and 6F show an exploded and partial cutaway views of a suture cartridge 660 suitable for use with MIS suture delivery tools in accordance with embodiments of the present invention. Cartridge 660 can be used to releasably hold one or more unidirectional self-retaining suture 600 with an anchor 602a-d such as described in FIGS. 6A-6D. In cartridge 660, one or more self-retaining suture systems 600 is arranged in a linear configuration. The linear configuration is suitable for shorter sutures which are often used in MIS surgery. For example, in one embodiment, self-retaining suture system 600 is, in some embodiments, approximately 70 mm in total length. Cartridge 660 would be approximately 70 mm in length to accommodate the 70 mm suture in the configuration of FIG. 6E. As shown in FIGS. 6E and 6F, cartridge 660 is approximately cylindrical and has a projection 662 on its proximal end for releasably engaging a suture delivery tool. Cartridge 660 has an opening 664 at its distal end for allowing access to the interior of cartridge 660. Adjacent opening 664 there are one or more needle docks 667 for releasably holding one or more needles 110. As shown in FIG. 6F one or more self-retaining suture system 600 can be contained within cartridge 660 with needles 110 releasably secured adjacent opening 664 by needle docks 666. Anchors 602a-d of self-retaining suture systems 600 are positioned towards the proximal end of the cartridge 660.

Multiple self-retaining suture systems 600 are, in some embodiments, loaded in a cartridge 660. As shown in FIG. 6E the self-retaining suture systems 600 are stacked and loaded through opening 664. Where multiple self-retaining suture systems 600 are loaded in a cartridge 600 they can be spaced from one another by dividers or the like to prevent entanglement. Cartridge 670 of FIG. 6G and/or dividers 669 have sufficient needle docks 667 for each of the needles 110. As shown in FIGS. 6E and 6F, multiple self-retaining suture systems 600 are separated from one another by dividers 669. Each of the plurality of self-retaining suture systems 600 can be, in some embodiments, removed individually from a cartridge 670. Cartridge 660 containing one or more self-retaining suture system 600 can be mounted to an endoscopic suture delivery tool as previously described for delivery of self-retaining suture systems 600 through a port to a desired location within a patient's body. In use, the surgeon may remove one self-retaining suture system 600 and its associated needle 110 and anchor 602a-d without disturbing the other self-retaining suture systems 600.

Figure 6G:
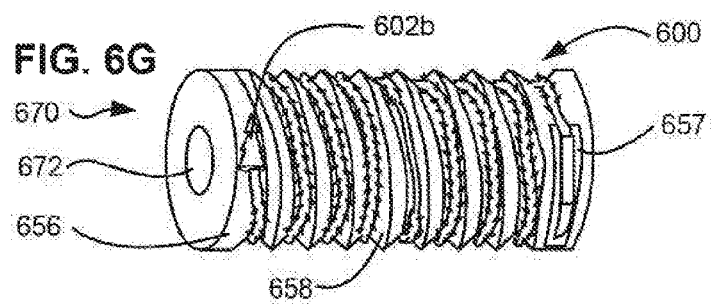
FIGS. 6G-6H show views of a cartridge/spool for holding one more of the alternative self-retaining suture systems of FIGS. 6A-6D.

FIG. 6G shows a cartridge 670 which includes spool 656 and a connector 672. Connector 672 allows cartridge 670 to be releasably attached to the distal end of a tool such as an endoscopic tool. Spool 656 includes a spiral groove 658 for releasably holding a unidirectional self-retaining suture 600 with an anchor 602a-d such as described in FIGS. 6A-6D. As shown in FIG. 6G, spool 656 also includes one or more needle docks 657 for supporting the needle 110 of self-retaining suture system 600. Needle 110 is releasable attached to needle dock 657. The needle 110 is removed from needle dock 657 to allow deployment of self-retaining suture system 600. In some embodiments, needle 110 is replaced in needle dock 657 to allow removal of needle 110 and any surplus self-retaining suture thread after deployment of self-retaining suture system 600.

Figure 6H:
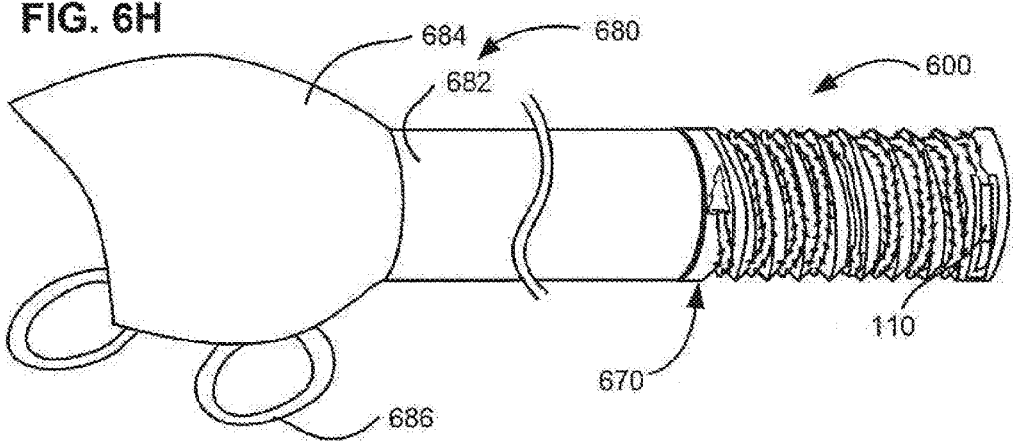

FIG. 6H shows cartridge 670 attached to the elongated member 682 of an endoscopic instrument 680 for insertion through a port into the body of a patient. A selection of sterile cartridges 670 is, in some embodiments, supplied for a procedure each supporting a different self-retaining suture system 100, 600. Thus, endoscopic suture delivery instrument 680 can be used by the surgeon or assistant to select and deliver multiple self-retaining suture systems 100, 600 in the course of a procedure. Handle 684 can be manipulated by a surgeon outside the body of a patient to deliver spool 656 to a desired site within the patient. In some embodiments, an actuator 686 is provided to control the attaching and releasing of the cartridge 670. In alternative embodiments spool 656 is fixed to the end of suture delivery instrument 680. Although a manual endoscopic instrument 680 is shown, cartridge 670 can also be delivered by a robotically-operated endoscopic tool as shown for example in FIG. 3A.

Suture delivery systems of the present invention include, in some embodiments, the systems, dispensers, devices and methods described below.

A suture dispenser, comprising:
  a self-retaining suture having an elongated suture body with a first segment having a first plurality of retainers disposed proximally to a first end, and a second segment having a second plurality of retainers disposed proximally to a second end;
  an elongated shaft;
  a spool coupled to a distal end of the elongated shaft, the self-retaining suture being releasably secured to the spool; and
  an actuator attached to a proximal end of the elongated shaft by which the dispenser is manipulated to introduce the spool and distal end of the elongated shaft through an access port into a surgical site within a patient.

The dispenser wherein:
  the self-retaining suture comprises a first needle at the first end and a second needle at the second end; and
  the spool comprises a first needle dock for the first needle and a second needle dock for the second needle.

The dispenser wherein:
  the spool comprises a plurality of suture containment regions to segregate the retainers of the first segment from the retainers of the second segment.

The dispenser wherein:
  the spool comprises a plurality of grooves to segregate the retainers of the first segment from the retainers of the second segment.

The dispenser wherein:
  the spool is releasably coupled to the distal end of the elongated shaft such that the spool is adapted to be replaced by a second spool.

The dispenser further comprising:
  a cover positioned over the spool and adapted to protect the self-retaining suture during introduction of the spool and distal end of the elongated shaft through an access port into a surgical site within a patient.

The dispenser further comprising:
  a cover positioned over the spool and adapted to protect the self-retaining suture during introduction of the spool and distal end of the elongated shaft through an access port into a surgical site within a patient; and
  wherein the cover can be opened to access the self-retaining suture.

The dispenser further comprising:
  a cover positioned over the spool and adapted to protect the self-retaining suture during introduction of the spool and distal end of the elongated shaft through an access port into a surgical site within a patient; and
  wherein the actuator is coupled to the cover and can open the cover within a patient to permit access to the self-retaining suture.

The dispenser wherein:
  the dispenser is provided with a machine-readable code to identify a characteristic of the self-retaining suture.

The dispenser wherein:
the spool includes a therapeutic agent to apply to the self-retaining suture.

The suture dispenser wherein:
said spool has a helical groove to releasably hold said self-retaining suture.

The suture dispenser wherein:
said spool has a groove to releasably hold said self-retaining suture.

The suture dispenser wherein:
said suture includes an elongated channel to releasably hold said self-retaining suture.

The suture dispenser wherein:
said suture dispense has a linear channel to releasably hold said self-retaining suture.

The suture dispenser wherein:
first retainers of said first plurality of retainers and second retainers of said second plurality of retainers all project in the same direction along the suture.

The suture dispenser wherein:
first retainers of said first plurality of retainers project in a first direction along said suture, and second retainers of said second plurality of retainers project in a second direction along the suture and wherein said first direction is different from said second direction.

The suture dispenser wherein:
said actuator is a handle.

The suture dispenser wherein:
said actuator is a mount that is adapted to mount said suture dispenser onto a robotic-assisted surgical tool.

The suture dispenser wherein:
said actuator is a mount that is adapted to mount said suture dispenser onto at least one of an endoscopic surgical tool and a laparoscopic surgical tool.

The suture dispenser wherein:
said spool has a diameter about 12 mm or less.

The suture dispenser wherein:
said spool has a diameter of about 8 mm or less.

The suture dispenser wherein:
said spool has a diameter of about 5 mm or less.

The suture dispenser wherein:
wherein said shaft is flexible.

The suture dispenser wherein:
said suture includes a pledget.

The suture dispenser wherein:
said suture dispenser is adapted to be operated by a telesurgical system.

The suture dispenser in combination with a telesurgical system.

The suture dispenser in combination with one of an endoscopic surgical tool, a robotic-assisted tool, and a laparoscopic surgical tool.

The suture dispenser wherein said dispenser is provided with a machine readable code to identify a characteristic of said suture, in combination with a telesurgical system with a code reader and a display, and wherein said code reader can read said code and said display can display a representation of said code.

The suture dispenser wherein said dispenser is provided with a machine readable code to identify a characteristic of said suture, in combination with a robotic-assisted tool with a code reader and a display, and wherein said code reader can read said code and said display can display a representation of said code.

The suture dispenser wherein said dispenser is provided with a machine readable code to identify one of or both of a static characteristic and a dynamic characteristic of said suture, in combination with a telesurgical system with a code reader and a display, and wherein said code reader can read said code and said display can display a representation of said code.

The suture dispenser in combination with a telesurgical system that can accept voice commands is order to at least one of select the spool and deploy the suture.

The suture dispenser wherein said dispenser can accept and dispense a plurality of spools.

The suture dispenser wherein said dispenser is a magazine that can accept and dispense a plurality of spools.

The suture dispenser wherein said actuator is an interface that is adapted to be releasably attached to one of a robotic-assisted system, a robot system and a telesurgical system.

A suture dispenser comprising:
a self-retaining suture;
a spool that is adapted to be releasably attached to a surgical tool; and
a channel in said spool that can selectively receive said self-retaining suture.

The suture dispenser wherein said channel is helical.

The suture dispenser wherein said channel is straight.

The suture dispenser including a cover to cover said spool with the self-retaining suture received in a channel of said spool.

The suture dispenser wherein said spool has a diameter of about 12 mm and less.

The suture dispenser wherein said spool has a diameter of about 8 mm and less.

The suture dispenser wherein said spool has a diameter of about 5 mm and less.

The suture dispenser wherein said suture has a pledget.

The suture dispenser wherein said dispenser has a machine readable code that can identify a characteristic of said suture.

The suture dispenser wherein said spool includes at least one needle dock and said suture includes at least one needle.

A suture dispenser, comprising:
a self-retaining suture having an elongated suture body with a first segment having a plurality of retainers disposed proximally to a first end, and a second segment having a plurality of retainers disposed proximally to a second end;
an endoscopic tool comprising an elongated tube;
a suture cartridge positioned within a distal end of the elongated tube the self-retaining suture being releasably secured to the suture cartridge; and
an interface attached to a proximal end of the elongated shaft by which the dispenser is manipulated to introduce the distal end of the elongated shaft through an access port into a surgical site within a patient.

The dispenser wherein:
the self-retaining suture comprises a first needle at the first end and a second needle at the second end; and
the suture cartridge comprises a first needle dock for the first needle and a second needle dock for the second needle.

The dispenser wherein:
the suture cartridge comprises a plurality of suture containment regions adapted to segregate the retainers of the first segment from the retainers of the second segment.

The dispenser wherein:
the suture cartridge is releasably coupled to suture dispenser such that the spool is adapted to be replaced by a second spool.

The dispenser further comprising a second self-retaining suture releasable secured to a second suture cartridge positioned with the elongate tube.

The dispenser wherein:
the elongate tube comprises a cover positioned over the spool to protect the self-retaining suture during introduction distal end of the elongated tube through an access port into a surgical site within a patient; and
wherein the cover can be opened within a patient to permit access to the self-retaining suture.

The dispenser further comprising an actuator adapted to move the cartridge out of the distal end of the elongate tube to permit access to the self-retaining suture.

The dispenser wherein:
the cartridge is provided with a machine-readable code adapted to identify a characteristic of the self-retaining suture for display to a surgeon.

The dispenser wherein:
the cartridge includes a therapeutic agent to apply to the self-retaining suture.

The dispenser wherein:
the interface is adapted to be releasably attached to a surgical robot.

A system for delivering suture to a surgical site within a patient with an endoscopic instrument, the system comprising:
a plurality of cartridges each loaded with a suture;
a cartridge selector that can select a cartridge having a selected suture; and
a cartridge actuator that can move the selected cartridge through the endoscopic instrument and exposing the selected cartridge to permit access to the self-retaining suture from within a surgical site within a patient.

The system wherein the system further comprises a surgical robot for positioning the endoscopic instrument and thereby positioning the selected cartridge within a patient.

The system wherein the selector is responsive to a voice command of a surgeon.

The system wherein the cartridge selection, comprises:
a housing external to the patient having a plurality of bays to receive the plurality of cartridges; and
an aligner that can align one of the plurality of bays and one of the plurality of cartridges with a lumen of the endoscopic instrument in order to deliver the surgical site within a patient.

The dispenser wherein:
said spool includes a plurality of suture containment regions that hold the suture and prevent the retainers from being repositioned.

The dispenser wherein:
said spool includes a plurality of suture containment regions that hold the suture and prevent the retainers from being repositioned.

The dispenser wherein:
said suture has acquired a memory set that including a plurality of loops about the diameter of said spool.

The dispenser wherein:
said suture has acquired a memory set that including a plurality of loops about the diameter of said spool.

The dispenser wherein:
said suture has acquired a memory set that including a plurality of loops about the diameter of said spool.

The dispenser wherein:
said suture has acquired a memory set that including a plurality of loops about the diameter of said spool.

The dispenser wherein:
said suture has acquired a memory set that including a plurality of loops about the diameter of said spool, which loops assist in tight radius suturing.

The dispenser wherein:
said suture has acquired a memory set that including a plurality of loops about the diameter of said spool, which loops assist in tight radius suturing.

The dispenser wherein:
said suture has acquired a memory set that including a plurality of loops about the diameter of said spool, which loops assist in tight radius suturing.

The dispenser wherein:
said suture has acquired a memory set that including a plurality of loops about the diameter of said spool, which loops assist in tight radius suturing.

A minimally invasive surgical method comprising:
delivering a cartridge to a surgical site, which cartridge includes a suture with self-retainers and a needle;
accessing the cartridge with an endoscopic tool;
using the endoscopic tool to remove the suture from the cartridge;
using the endoscopic tool to sew tissue with the suture.

The method wherein:
said delivering step includes delivering said cartridge with one of an endoscopic tool, a laparoscopic tool, a robotically assisted tool, and a telesurgical tool.

The method wherein:
said delivering step includes paying out the suture from the cartridge.

The method wherein:
said delivering step includes paying out the suture from the cartridge.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as is, in some embodiments, included within the spirit and scope of the invention as defined by the following claims.

What is claimed is:

1. A suture dispenser, comprising:
a self-retaining suture having an elongated suture body with a first segment having a first plurality of retainers disposed proximally to a first end, and a second segment having a second plurality of retainers disposed proximally to a second end and first and second needles disposed at the first and second ends respectively;
an elongated shaft;
a spool positioned at a distal end of the elongated shaft, the spool comprising first and second needle docks adjacent to each other at a distal end thereof, the self-retaining suture being releasably secured to the spool and the first and second needles being releasably secured to one of the first and second needle docks respectively; and
an actuator attached to a proximal end of the elongated shaft by which the dispenser is manipulated to introduce the spool and distal end of the elongated shaft through an access port into a surgical site within a patient.

2. The dispenser of claim 1, wherein:

the spool comprises a plurality of suture containment regions to segregate the retainers of the first segment from the retainers of the second segment.

3. The dispenser of claim 1, wherein:

the spool is releasably coupled to the distal end of the elongated shaft such that the spool is adapted to be replaced by a second spool.

4. The dispenser of claim 1, wherein:

the dispenser is provided with a machine-readable code to identify a characteristic of the self-retaining suture.

5. The suture dispenser of claim 1 wherein:

said spool has a diameter about 12 mm or less.

6. The suture dispenser of claim 1 in combination with a telesurgical system.

7. The suture dispenser of claim 1 wherein said dispenser can accept and dispense a plurality of spools.

8. A suture dispenser, comprising:

a self-retaining suture having an elongated suture body with a first segment having a plurality of retainers disposed proximally to a first end, and a second segment having a plurality of retainers disposed proximally to a second end and first and second needles disposed at the first and second ends respectively;

an endoscopic tool comprising an elongated tube;

a suture cartridge positioned within a distal end of the elongated tube, the suture cartridge comprising first and second needle docks at a distal end thereof, the self-retaining suture being releasably secured to the suture cartridge and the first and second needles being releasably secured to one of the first and second needle docks respectively; and an interface attached to a proximal end of the elongated shaft by which the dispenser is manipulated to introduce the distal end of the elongated shaft through an access port into a surgical site within a patient.

* * * * *